(12) United States Patent
Reiner

(10) Patent No.: US 11,179,525 B2
(45) Date of Patent: Nov. 23, 2021

(54) INHALER ADAPTER FOR PATIENT BREATHING TUBE ASSEMBLY AND METHOD

(71) Applicant: Instrumentation Industries, Inc., Bethel Park, PA (US)

(72) Inventor: Steven C. Reiner, Pittsburgh, PA (US)

(73) Assignee: Instrumentation Industries, Inc., Bethel Park, PA (US)

( * ) Notice: Subject to any disclaimer, the term of this patent is extended or adjusted under 35 U.S.C. 154(b) by 409 days.

(21) Appl. No.: 15/926,420

(22) Filed: Mar. 20, 2018

(65) Prior Publication Data

US 2018/0272084 A1 Sep. 27, 2018

Related U.S. Application Data

(60) Provisional application No. 62/476,609, filed on Mar. 24, 2017.

(51) Int. Cl.
*A61M 15/00* (2006.01)
*A61M 16/14* (2006.01)
*A61M 16/08* (2006.01)

(52) U.S. Cl.
CPC ...... *A61M 15/0021* (2014.02); *A61M 15/009* (2013.01); *A61M 15/0065* (2013.01); *A61M 16/0833* (2014.02); *A61M 16/147* (2014.02); *A61M 2202/0007* (2013.01)

(58) Field of Classification Search
CPC .... A61M 11/00–08; A61M 15/00–085; A61M 16/08–0858; A61M 16/0875–0891; A61M 16/14–147; A61M 2202/0007; A61M 2016/003–0042; A61M 2205/27–276; A61M 2205/3561; A61M 2205/52; A61M 2205/584; A61M 2205/587; A61M 2205/6054;
(Continued)

(56) References Cited

U.S. PATENT DOCUMENTS

| D655,411 S | 3/2012 | Schroeder et al. |
| D679,008 S | 3/2013 | Schroeder et al. |
| 9,084,864 B1 | 7/2015 | Schroeder et al. |

(Continued)

OTHER PUBLICATIONS

FDA 510K 101857, Special 510(k) Summary for RTC 24-VP Metered Dose Inhaler Adapter, Instrumentation Industries, Inc., Jul. 2, 2010, 5 pages.
(Continued)

*Primary Examiner* — Elliot S Ruddie
(74) *Attorney, Agent, or Firm* — The Webb Law Firm

(57) ABSTRACT

An inline adapter is provided including an elongated hollow body having an open first end configured to be connected to an inspiratory port of a patient ventilation assembly, an open second end opposite the first end, and a sidewall extending therebetween defining an airflow channel. The adapter also includes an inhaler port extending from the open second end of the adapter body configured to be connected to an inhaler, and an inspiratory branch having an open first end extending from an opening in the sidewall of the adapter body and an open second end configured to be connected to an inspiratory limb of the ventilation assembly. A longitudinal central axis of the inspiratory branch is angled relative to a longitudinal central axis of the adapter body.

21 Claims, 15 Drawing Sheets

(58) Field of Classification Search
CPC ........... A61M 2205/82–8206; A61M 16/0866;
B05B 17/00–0646; B05B 17/0692
USPC ...................................... 128/203.12–203.16
See application file for complete search history.

(56) References Cited

U.S. PATENT DOCUMENTS

| | | | | |
|---|---|---|---|---|
| 2010/0071688 A1* | 3/2010 | Dwyer | .............. | A61M 16/0816 128/200.18 |
| 2011/0247616 A1* | 10/2011 | Von Hollen | ...... | A61M 16/0816 128/203.12 |
| 2011/0259323 A1* | 10/2011 | Crosby | ............... | A61M 15/009 128/200.14 |
| 2013/0081617 A1* | 4/2013 | Cavendish | ........ | A61M 16/0816 128/203.12 |

OTHER PUBLICATIONS

FDA 510K K091111, 510(k) Summary for RTC 24-V MDI Adapter and RTC 24-V MDI Adapter Kit, Instrumentation Industries, Inc., Nov. 25, 2009, 7 pages.
FDA 510K K140919, Indications for Use, Section 5—510(k) Summary, Trudell Medical International, Aug. 15, 2014, 8 pages.
MDI Adapter Installation and Usage Directions for RTC 24-V and RTC 24-V Kit, Nov. 2009, 2 pages.

* cited by examiner

INHALER ADAPTER FOR PATIENT BREATHING TUBE ASSEMBLY AND METHOD

CROSS REFERENCE TO RELATED APPLICATION

The present application claims priority from U.S. Provisional Patent Application No. 62/476,609, filed on Mar. 24, 2017, which is incorporated herein by reference in its entirety.

BACKGROUND

Technical Field

The present disclosure relates to methods and devices for providing a metered dose of aerosolized medication to a patient and, in particular, to an adapter for joining a medication-dispensing inhaler to an inline patient breathing or ventilation assembly.

Background

Aerosolized medication is provided to patients to treat respiratory conditions and breathing disorders including but not limited to asthma, emphysema, and chronic obstructive pulmonary disease (COPD). Traditionally, such medications are provided using a medication inhaler (e.g., a metered dose inhaler) comprising a canister of pressurized medication, a discharge port for expelling the medication from the inhaler, and a mouthpiece. The patient places the mouthpiece between his/her lips and actuates the inhaler to discharge the medication into his/her mouth through the inhaler discharge port. As the medication is being dispensed, the patient inhales to draw the discharged fluid medication into his/her lungs. In some examples, aerosolization chambers can be attached to the inhaler mouthpiece to improve dispersion of the released medication. For some patients, aerosolization chambers help to ensure that dispensed medication is drawn through the mouth and into the patient's lungs.

Adapters and connectors for interfacing a metered dose inhaler to a patient breathing tube or ventilation assembly are also known. Exemplary adapters include the RTC 24-V adapter and the RTC 22-D adapter manufactured by Instrumentation Industries, Inc. of Bethel Park, Pa. The RTC 24-V adapter is illustrated in FIGS. 1A and 1B. The RTC 24-V adapter 10 comprises a T-shaped body 12 configured to be connected between a patient wye 2 and a patient endotracheal tube 4 as shown in FIG. 1B. The adapter 10 further comprises an inhaler port 14 extending transversely from the adapter body 12. A metered dose inhaler 6 can be mounted to the inhaler port 14 as shown in FIG. 1B. A dose of medication expelled from the inhaler 6 is dispersed in an airflow channel 16 of the adapter 10 through a conduit 18. The dispersed medication is provided to the patient through the endotracheal tube 4.

However, there is a need for an inline adapter for a patient breathing tube assembly that can provide straight line delivery therethrough of an aerosolized medicament received from an inhaler aerosol discharge port or nozzle into a patient's inhalation breathing tube. For example, the adapter can be configured to accommodate a Combivent® Respimat® inhaler system including a cartridge containing ipratropium bromide and albuterol.

SUMMARY

Non-limiting examples of the present invention will now be described in the following numbered clauses:

Clause 1: An inline adapter, comprising: an elongated hollow body comprising an open first end configured to be connected to an inspiratory port of a patient ventilation assembly, an open second end opposite the first end, and a sidewall extending therebetween defining an airflow channel; an inhaler port extending from the open second end of the adapter body configured to be connected to an inhaler; and an inspiratory branch comprising an open first end extending from an opening in the sidewall of the adapter body and an open second end configured to be connected to an inspiratory limb of the ventilation assembly, wherein a longitudinal central axis of the inspiratory branch is angled relative to a longitudinal central axis of the adapter body.

Clause 2: The adapter of Clause 1, wherein the longitudinal central axis of the inspiratory branch forms an angle of between about 30 degrees and about 60 degrees relative to the longitudinal central axis of the adapter body.

Clause 3: The adapter of Clause 1 or Clause 2, wherein the longitudinal central axis of the inspiratory branch forms an angle of about 45 degrees relative to the longitudinal axis of the adapter body.

Clause 4: The adapter of any one of Clauses 1-3, wherein the inhaler port comprises an elongated sidewall extending from the second end of the adapter body, the sidewall configured to be received within a mouthpiece of the inhaler and to cover air vents on the inhaler.

Clause 5: The adapter of Clause 4, wherein the sidewall of the inhaler port comprises an elliptical cross section.

Clause 6: The adapter of Clause 5, wherein the cross section of an elliptical opening has a major external diameter D4 ranging from about 0.5 inches to about 1.25 inches.

Clause 7: The adapter of any one of Clauses 1-6, wherein the inhaler port comprises an interior wall covering the open second end of the adapter body, the interior wall comprising an opening configured to align with a discharge port of the inhaler to permit fluid discharged from the inhaler to pass into the airflow channel of the adapter body.

Clause 8: The adapter of any one of Clauses 1-7, wherein the open first end of the adapter body is configured to receive an inspiratory port of a patient wye of the ventilation assembly.

Clause 9: The adapter of any one of Clauses 1-8, wherein the open second end of the inspiratory branch of the adapter is configured to be inserted in an open end of the inspiratory limb of the patient ventilation assembly.

Clause 10: The adapter of any one of Clauses 1-9, wherein an outer diameter of the open second end of the inspiratory branch of the adapter is about equal to an inner diameter of the open first end of the adapter body.

Clause 11: The adapter of any one Clauses 1-10, wherein a total longitudinal length of the adapter ranges from about 2 inches to about 4 inches.

Clause 12: The adapter of any one Clauses 1-11, wherein a length of a longest longitudinal side of the inspiratory branch ranges from about 1 inches to about 2.5 inches.

Clause 13: The adapter of any one of Clauses 1-12, wherein the opening in the sidewall of the adapter body extending to the inspiratory branch is an elliptical opening.

Clause 14: The adapter of any one of Clauses 1-13, further comprising a cap removably connected to the inhaler port.

Clause 15: The adapter of Clause 14, wherein the cap comprises a thermoplastic rubber material.

Clause 16. A ventilation assembly for providing breathing air and aerosolized medication to a patient, comprising: an inspiratory limb comprising medical tubing configured to be connected to an outflow port of a mechanical ventilator device; an expiratory limb comprising medical tubing configured to be connected to an inflow port of the ventilator device; a patient wye comprising a patient port connected to a patient portion of the ventilation assembly, an expiratory port connected to the expiratory limb, and an inspiratory port; and an inline aerosol adapter connected between the inspiratory port of the patient wye and the inspiratory limb, the adapter comprising: an elongated hollow body comprising an open first end connected to the inspiratory port of the patient wye, an open second end opposite the first end, and a sidewall extending therebetween defining an airflow channel in fluid communication with an airflow channel of the patient wye; an inhaler port extending from the open second end of the adapter body configured to be connected to an inhaler; and an inspiratory branch comprising an open first end extending from an opening in the sidewall of the adapter body and an open second end connected to the inspiratory limb, wherein a longitudinal central axis of the inspiratory branch is angled relative to a longitudinal central axis of the adapter body.

Clause 17: The assembly of Clause 16, wherein a longitudinal central axis of the expiratory limb is substantially parallel to the longitudinal axis of the adapter body.

Clause 18: The assembly of Clause 16 or Clause 17, further comprising the inhaler, wherein the inhaler comprises a single-dose inhaler or a multi-dose inhaler.

Clause 19: The assembly of Clause 18, wherein the multi-dose inhaler comprises an indicator for indicating doses of medication remaining in the inhaler.

Clause 20: The assembly of Clause 18 or Clause 19, wherein the inhaler comprises air vents and wherein the inhaler port of the adapter covers the air vents when the inhaler is connected to the inhaler port.

Clause 21: A method of providing aerosolized medication to a patient through a patient ventilation assembly, comprising: attaching an inline adapter between an inspiratory port of a patient wye and an inspiratory limb of a ventilation assembly comprising tubing configured to be connected to a ventilator, wherein the adapter comprises: an elongated hollow body comprising an open first end configured to be connected to the inspiratory port of the patient wye, an open second end opposite the first end, and a sidewall extending therebetween defining an airflow channel; an inhaler port extending from the open second end of the adapter body configured to be connected to an inhaler; and an inspiratory branch comprising an open first end extending from an opening in the sidewall of the adapter body and an open second end configured to be connected to the inspiratory limb of the ventilation assembly, wherein a longitudinal central axis of the inspiratory branch is angled relative to a longitudinal central axis of the adapter body; connecting the inhaler to the inhaler port of the adapter; actuating the ventilator to provide breathing air to the patient through the ventilation assembly and adapter; and actuating a dose release actuator of the inhaler to provide aerosolized medication to the patient through the adapter and ventilation assembly.

BRIEF DESCRIPTION OF THE DRAWINGS

These and other features and characteristics of the present disclosure, as well as the methods of operation and functions of the related elements of structures and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limit of the invention.

Further features and other examples and advantages will become apparent from the following detailed description made with reference to the drawings in which.

DETAILED DESCRIPTION OF THE INVENTION

Figure 1A:
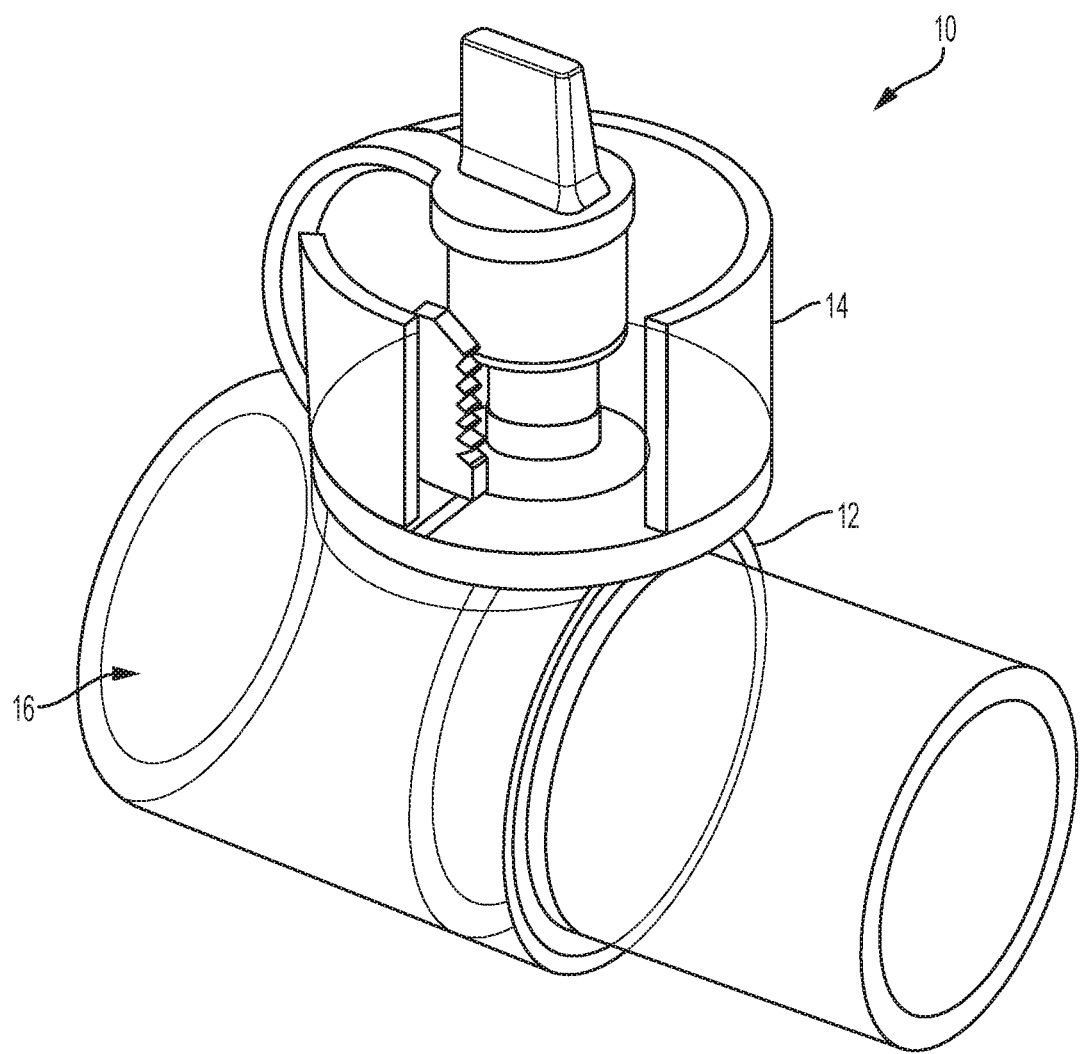
FIG. 1A is a perspective view of a prior art metered dose inhaler adapter.
Figure 1B:
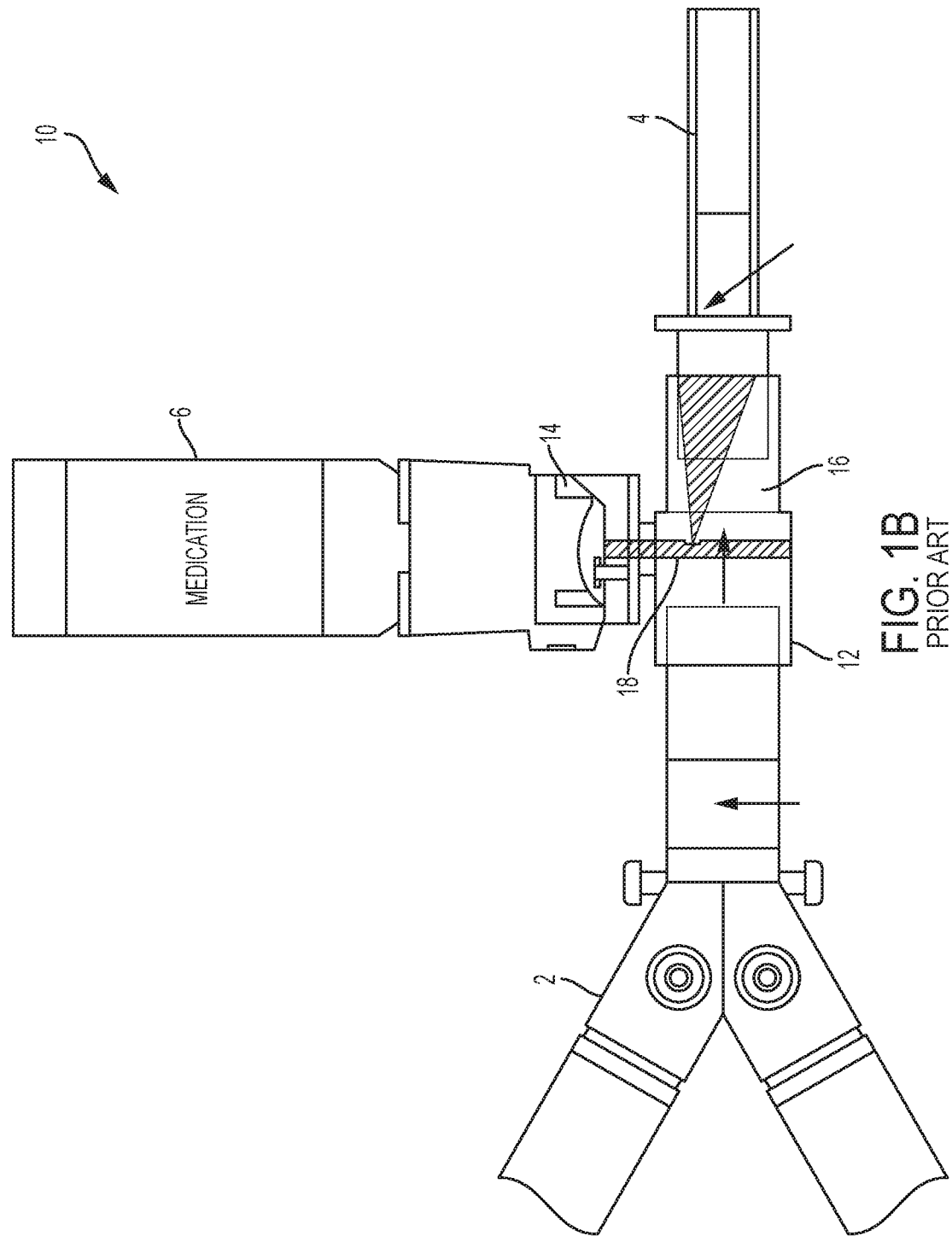
FIG. 1B is a schematic drawing of the prior art metered dose inhaler adapter of FIG. 1A connected to a patient ventilation assembly and inhaler.
Figure 2A:
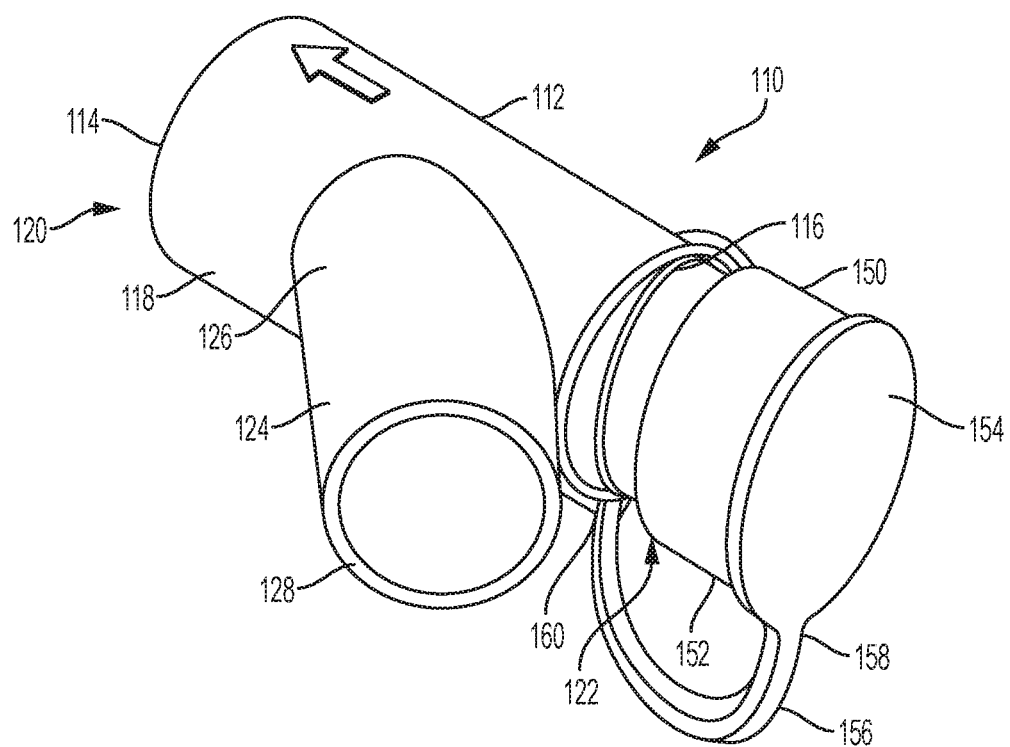
FIGS. 2A and 2B are perspective views of an inline adapter according to an example of the present disclosure.
Figure 2B:
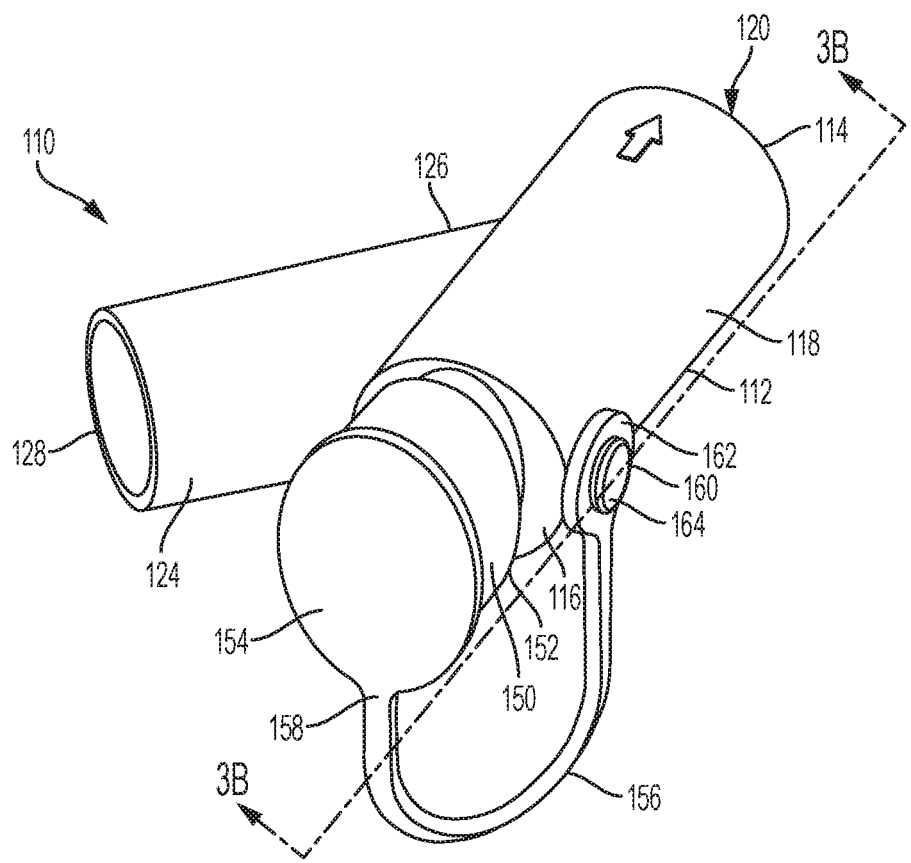

As used herein, the singular form of "a", "an", and "the" include plural referents unless the context clearly states otherwise.

As used herein, the terms "right", "left", "top", and derivatives thereof shall relate to the invention as it is oriented in the drawing figures. The term "proximal" refers to the portion of a medical device or assembly which is closest to and/or in contact with the patient. The term "distal" refers to the opposite end of the medical device or assembly from the proximal end. Thus, the term "distal" refers to a portion of a medical device or assembly which is farthest away from the patient. However, it is to be understood that the invention can assume various alternative orientations and, accordingly, such terms are not to be considered as limiting. Also, it is to be understood that the invention can assume various alternative variations and stage sequences, except where expressly specified to the contrary. It is also to be understood that the specific devices and processes illustrated in the attached drawings, and described in the following specification, are examples. Hence, specific dimensions and other physical characteristics related to the embodiments disclosed herein are not to be considered as limiting.

Unless otherwise indicated, all numbers expressing quantities of ingredients, reaction conditions, dimensions, physical characteristics, and so forth used in the specification and claims are to be understood as being modified in all instances by the term "about." Unless indicated to the contrary, the numerical parameters set forth in the following specification and attached claims are approximations that can vary depending upon the desired properties sought to be obtained by the present invention.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

Also, it should be understood that any numerical range recited herein is intended to include all sub-ranges subsumed therein. For example, a range of "1 to 10" is intended to include any and all sub-ranges between and including the recited minimum value of 1 and the recited maximum value of 10. That is, all subranges beginning with a minimum value equal to or greater than 1 and ending with a maximum value equal to or less than 10, and all subranges in between, e.g., 1 to 6.3, or 5.5 to 10, or 2.7 to 6.1.

As used herein, "aerosol" means a colloid of fine solid particles or liquid droplets, such as for example particles or droplets of a drug, medication or medicament, in air or another gas.

According to an example of the disclosure, an inline adapter 110 for a patient ventilation system or line, breathing tube, or patient ventilation assembly 200 is disclosed herein. The inline adapter 110 allows a user to mount or connect an inhaler 250, such as a metered dose inhaler, to the ventilation line or breathing tube, such that a dose of medication dispensed by the inhaler 250 can be delivered to a patient through the breathing tube. The medication to be delivered to the patient can be any aerosolizable medication, such as, for example, an aerosolized mixture of ipratropium bromide and albuterol.

Figure 7:
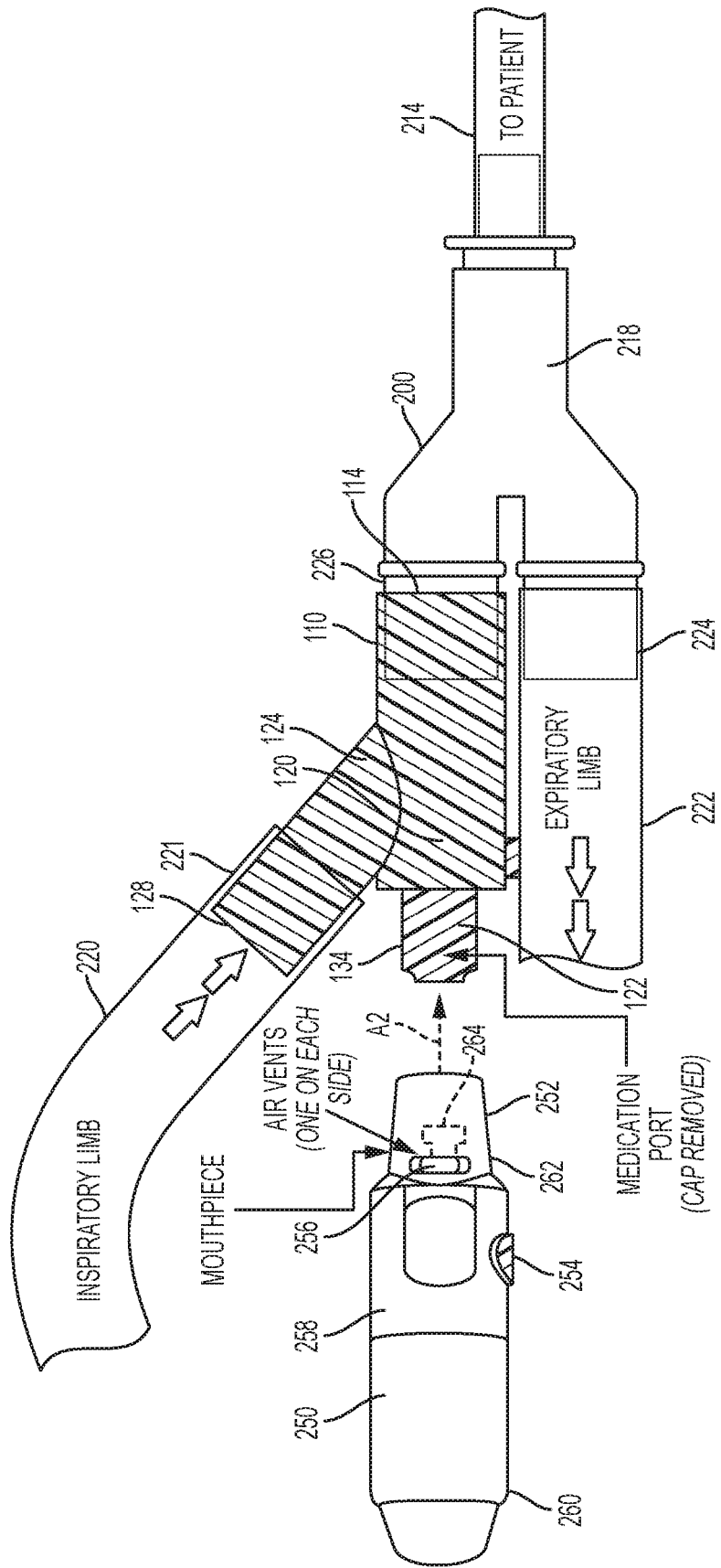
FIG. 7 is a schematic drawing of the assembly of FIGS. 4A and 4B prior to connecting the inhaler to the adapter.

As shown in FIG. 7, the inhaler 250 generally comprises a plastic housing 258, a pressurized canister or cartridge 260 containing one or more doses of a medication fluid to be delivered to a patient, and a mouthpiece 252 extending from the housing 258 having an elliptical sidewall 262 adapted to be placed in a patient's mouth. The mouthpiece 252 surrounds or encloses one or more discharge ports 264 (shown in phantom). One or more doses of aerosolized medication can be expelled through the discharge port 264 from the canister or cartridge 260. In some examples, the mouthpiece 252 comprises one or more vent holes 256 located on the annular sidewall 262 of the mouthpiece 252. The inhaler 250 further comprises a drug release mechanism or actuator or button 254. In some examples, the drug release mechanism is primed for dosing by rotating or twisting the inhaler housing 258. In some examples, the drug is released by pressing the button 254 or actuator which, when pressed or triggered, causes the inhaler 250 to automatically dispense the medication. In some examples, the inhaler system can be a Combivent® Respimat® inhaler system including a cartridge containing ipratropium bromide and albuterol. The Combivent® Respimat® inhaler is available from Boehringer Ingelheim Pharmaceuticals, Inc. of Ingelheim, Germany. Any inhaler can be used with the adapter of the present invention, as long as the connector on the adapter is configured to match the configuration of the drug release mechanism of the inhaler, subject to appropriate regulatory approval if necessary.

Figure 8:
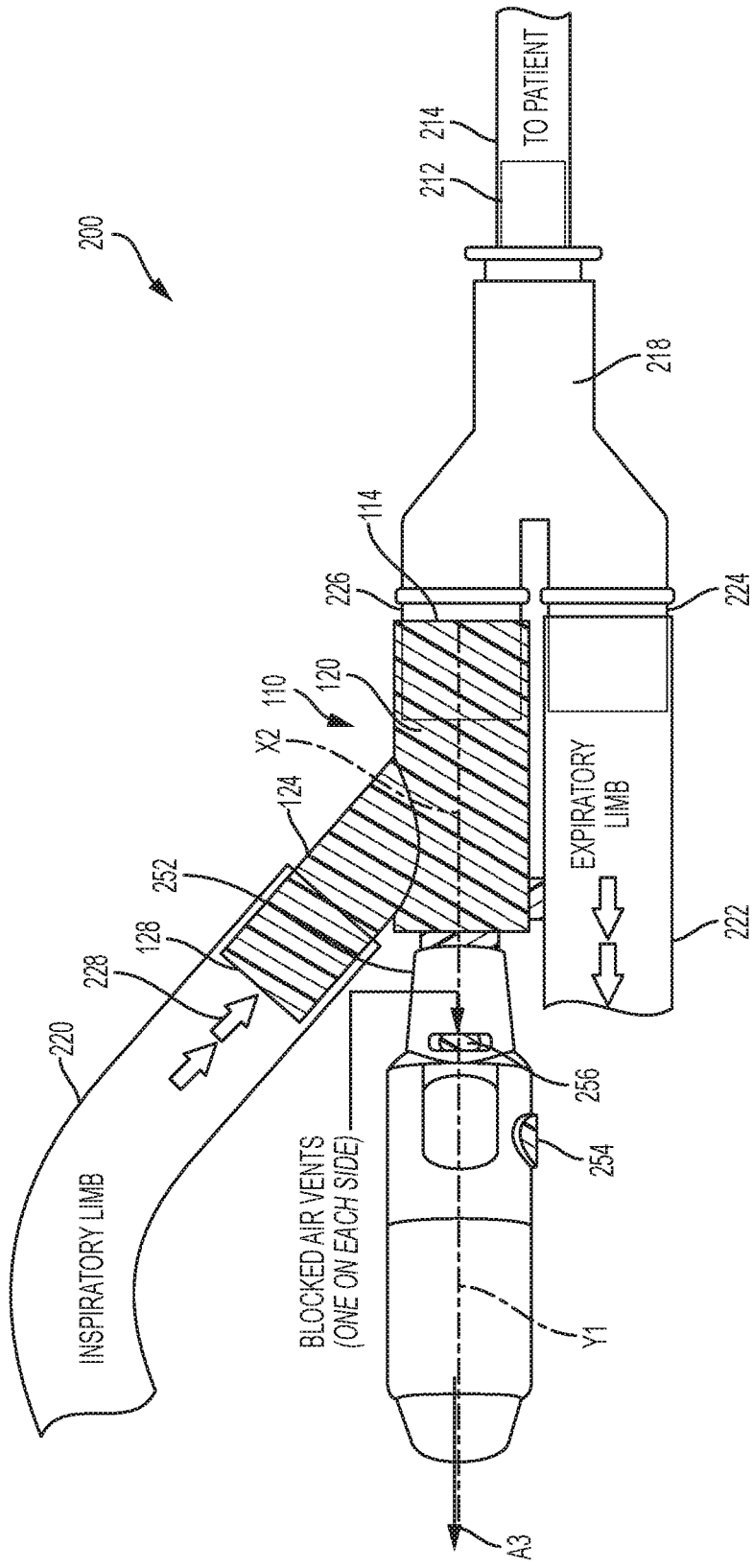
FIG. 8 is a schematic drawing of the assembly of FIGS. 4A and 4B in an in-use configuration.
Figure 9:
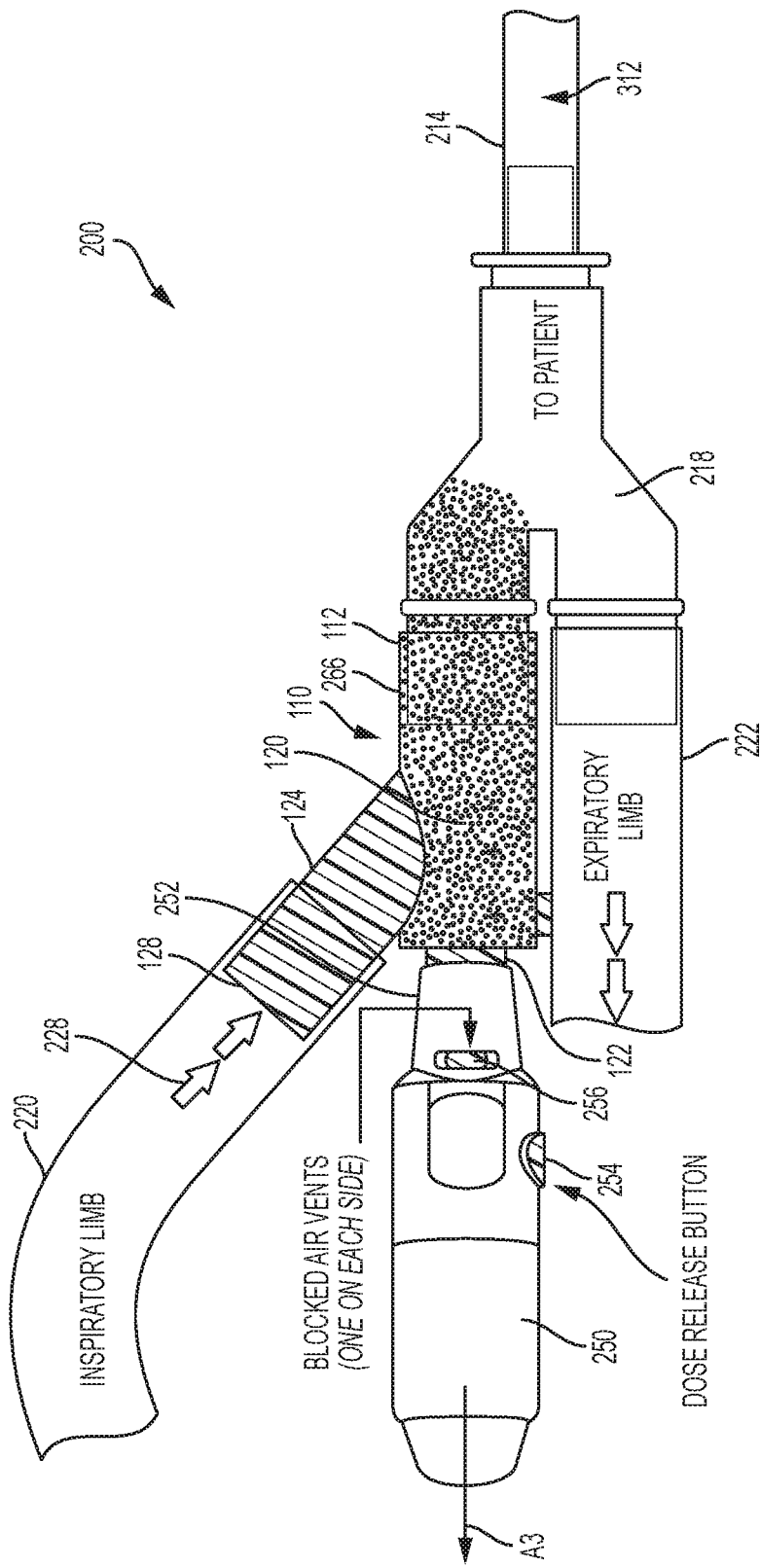
FIG. 9 is another schematic drawing of the assembly of FIGS. 4A and 4B in an in-use configuration, illustrating dispensing of an aerosolized dose of medication in the assembly.

The adapter 110 of the present disclosure can facilitate delivery of the dose of dispensed medication which is delivered to the patient. In order to facilitate medication distribution, in some configurations, the longitudinal central axis Y1 of the inhaler is coextensive with a longitudinal central axis X2 of the adapter, as shown in FIG. 8. As such, the inhaler 250 projects the aerosolized medication substantially straight or inline through the adapter body 112, as shown in FIG. 9. In other embodiments, the longitudinal central axis Y1 of the inhaler 250 may be angled with respect to the longitudinal central axis X2 of the adapter 110, for example, by up to about 5 degrees. Further, in some examples, the adapter 110 is positioned in the ventilation assembly 200 at a position distal to a patient wye 218 or connector. As shown in FIG. 9, the adapter 110 is not exposed to exhaled air which could cause backflow of dispersed medication. Instead, medication dispersed from the inhaler 250 is exposed only to inspiratory air 228 which directs the dispersed medication towards the patient.

Figure 5:
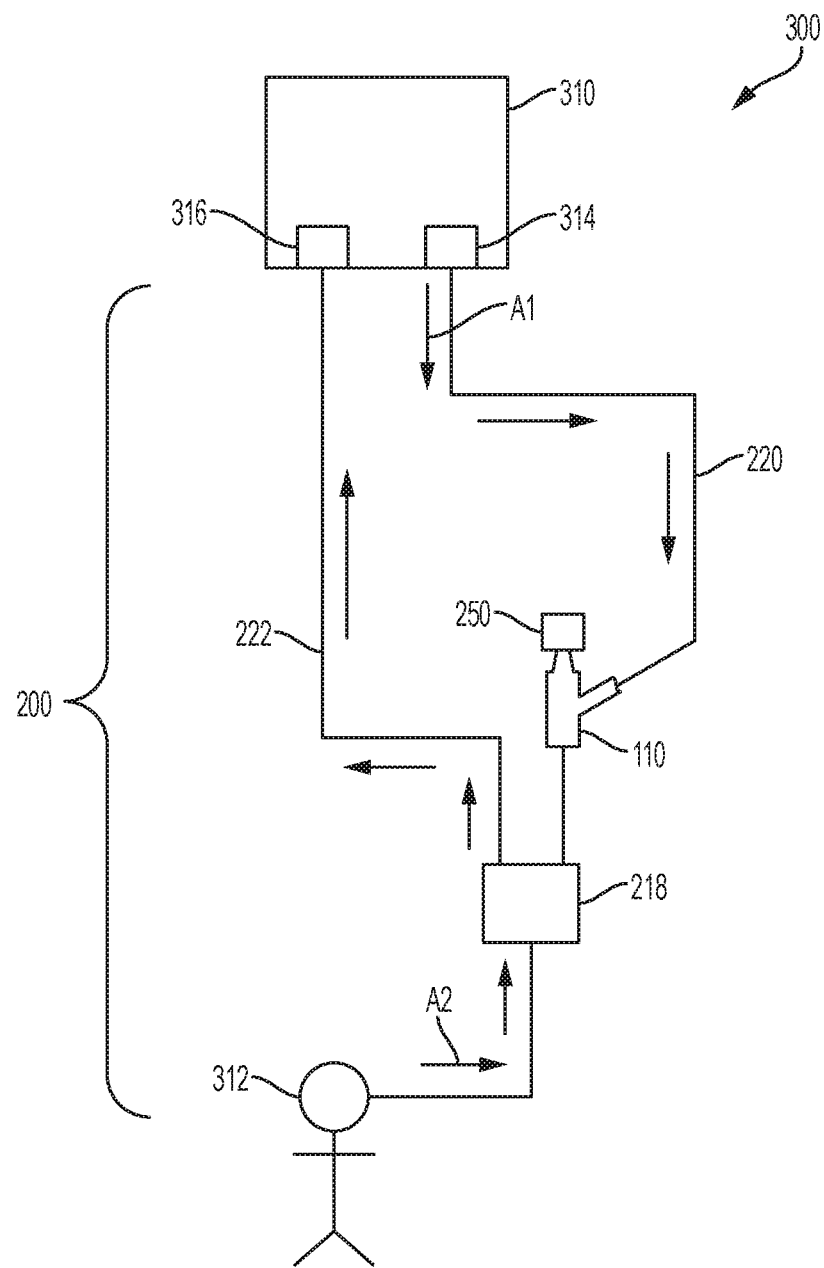
FIG. 5 is a schematic drawing of a breathing circuit including the adapter and ventilation assembly of FIGS. 4A and 4B.

In some examples, as shown in FIG. 5, a breathing circuit 300 comprising a ventilation assembly 200 or breathing tube for providing inspiratory air from a mechanical ventilator 310 to a patient 312 is provided. Non-limiting examples of suitable ventilators include a Puritan Bennett™ 840 ventilator available from Medtronic Inc., Dräger Evita Infinity® V500 ventilator available from Drägerwerk AG & Co. KGaA and Respironics V200 ventilator available from Philips. As shown in FIG. 8, the assembly 200 can comprise: a patient portion 212, such as an endotracheal tube, a nasotracheal tube, a tracheal tube, or any combination thereof; a branched connector or patient wye 218 extending from the patient portion 212; and inspiratory limb 220 and expiratory limb 222 extending from respective ends or ports of the patient wye 218 or branched connector. The inline aerosol adapter 110 of the present disclosure is mounted on or connected to the inhalation port or end of the patient wye 218. As described herein, the adapter 110 connects the inhaler 250 to the ventilation assembly 200 so that a metered dose of aerosolized medication dispensed from the inhaler 250 through the adapter 110 is provided to the patient 312 through the patient portion 212.

Inline Aerosol Adapter

An exemplary adapter 110 configured to be connected to a ventilation assembly 200 for providing a dose of an aerosolized medication expelled from a metered dose inhaler 250 to a patient is illustrated in FIGS. 2A-4B and 6-9. The adapter 110 generally comprises a tubular structure mounted at an angle relative to another elongated tubular structure to form a Y-shaped connector. For example, the adapter 110 may comprise a main body portion 112 formed from an elongated tube or hollow member and a second tube or elongated hollow member in fluid communication with and extending at an angle from the main body.

Figure 3B:
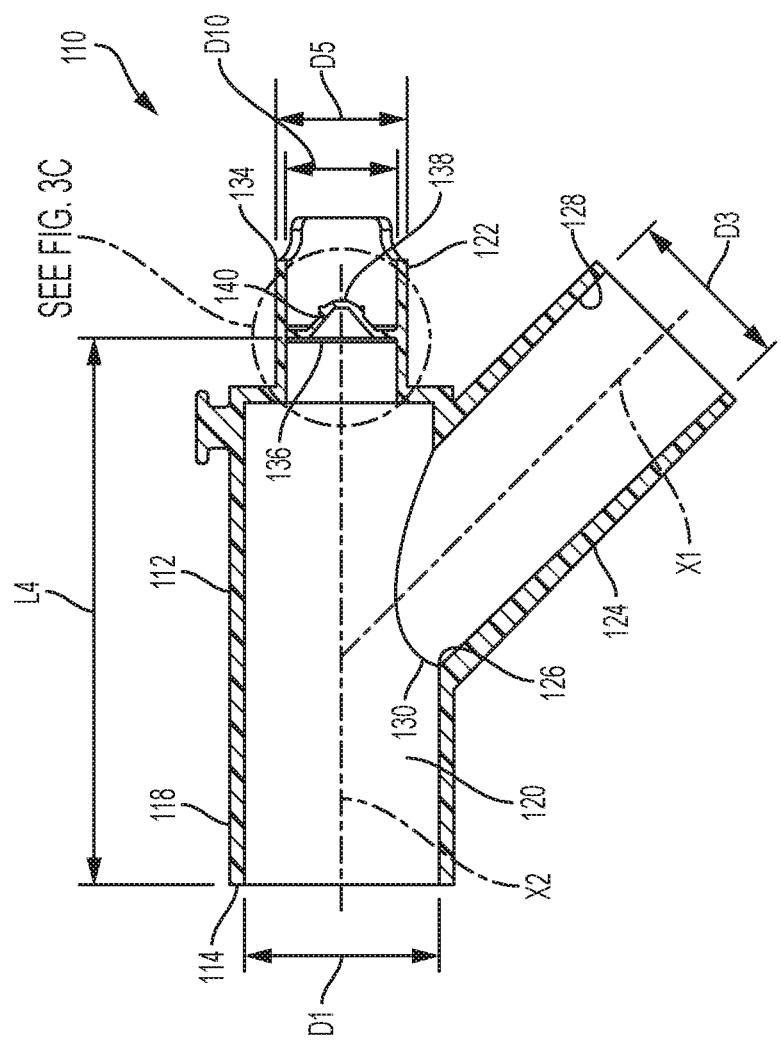
FIG. 3B is a cross sectional view of the adapter of FIG. 2B taken through a plane extending along line 3B-3B of FIG. 2B.
Figure 3A:
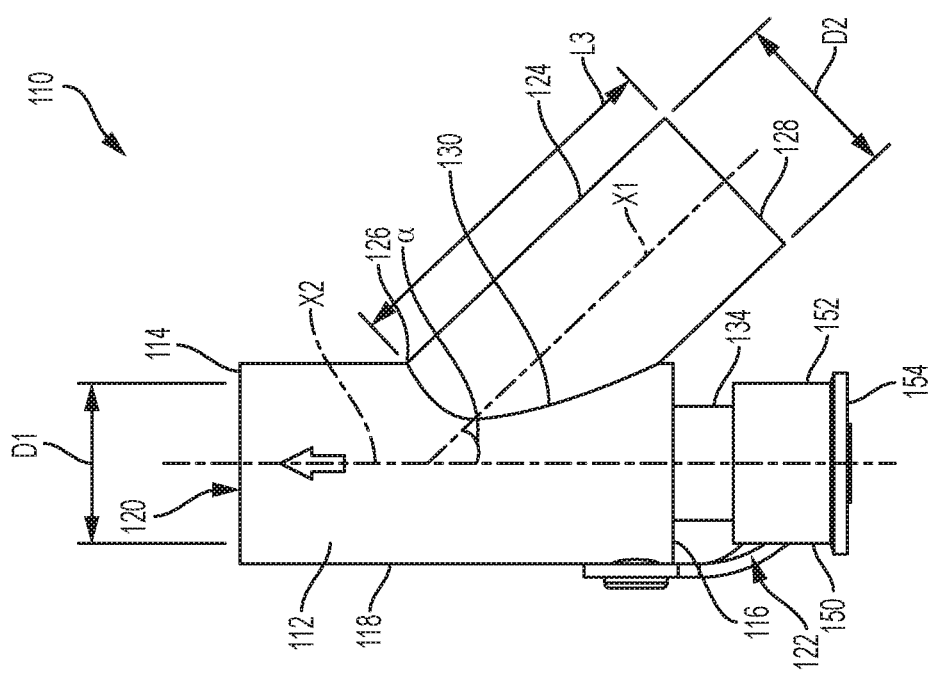
FIG. 3A is a top view of the adapter of FIGS. 2A and 2B.
Figure 3C:
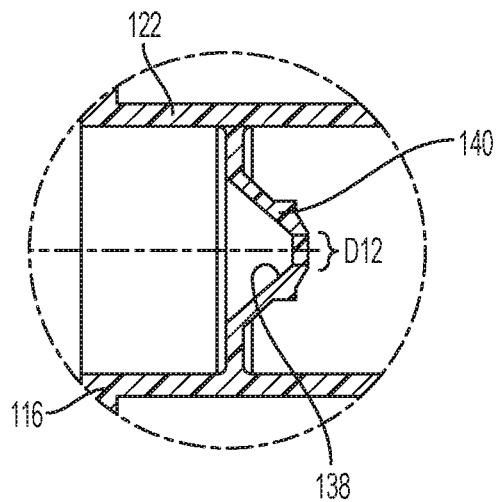
FIG. 3C is an enlarged view view of a portion of the adapter taken from area "3C" shown in FIG. 3B.
Figure 3D:
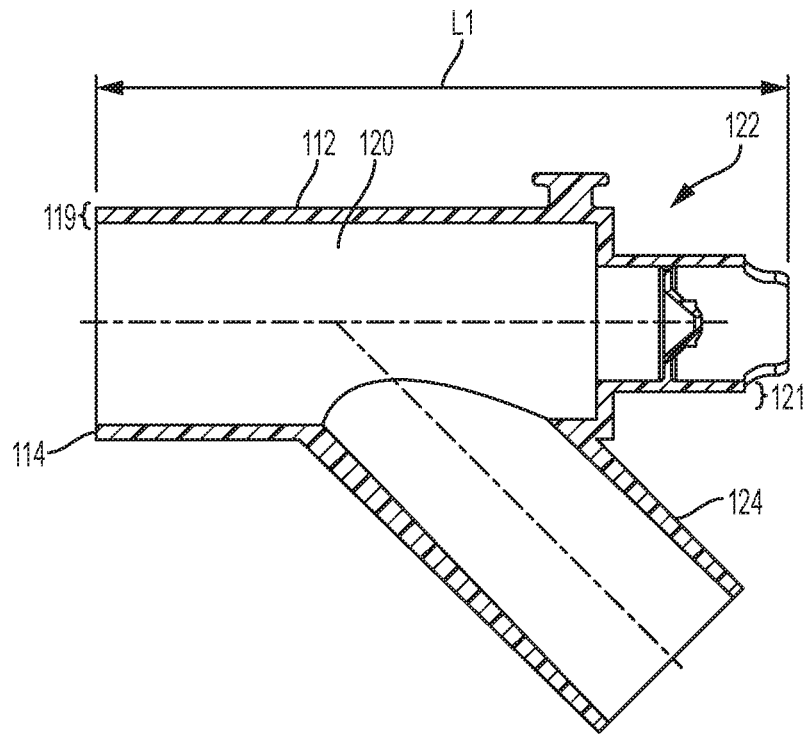
FIG. 3D is a cross sectional view of the adapter of FIG. 2B taken through a plane extending along line 3B-3B of FIG. 3B.
Figure 3F:
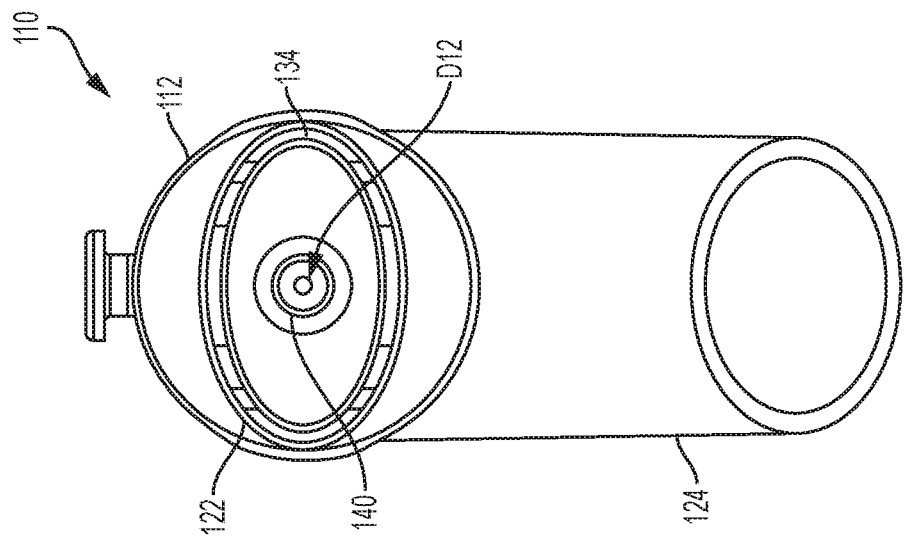
FIG. 3F is a front view of the adapter of FIG. 2B with the cap removed.
Figure 3E:
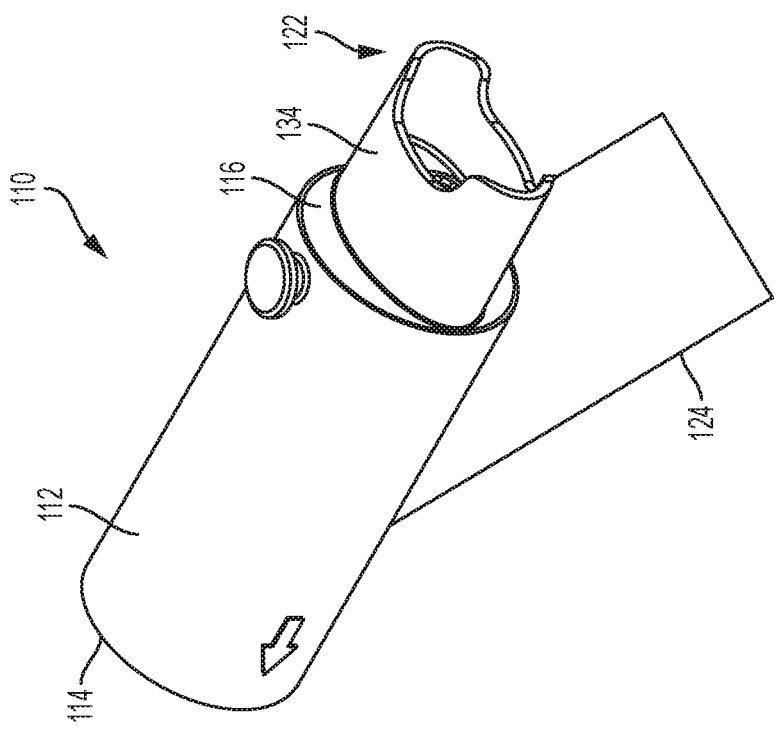
FIG. 3E is a perspective view of the adapter of FIG. 2B with the cap removed.
Figure 3G:
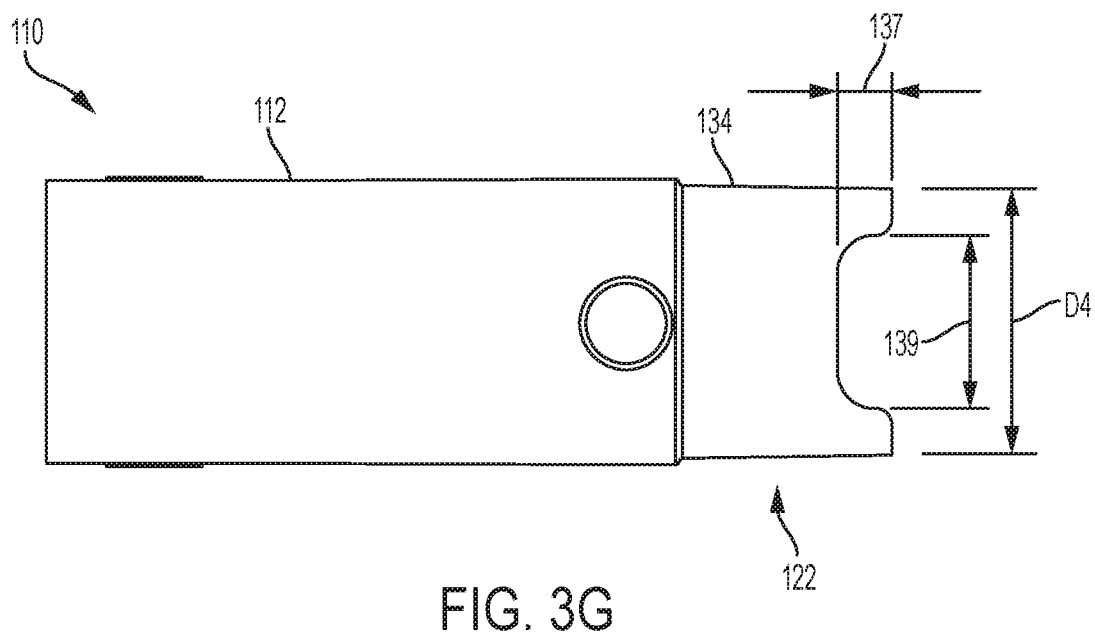
FIG. 3G is a side view of the adapter of FIG. 2B with the cap removed.
Figure 3H:
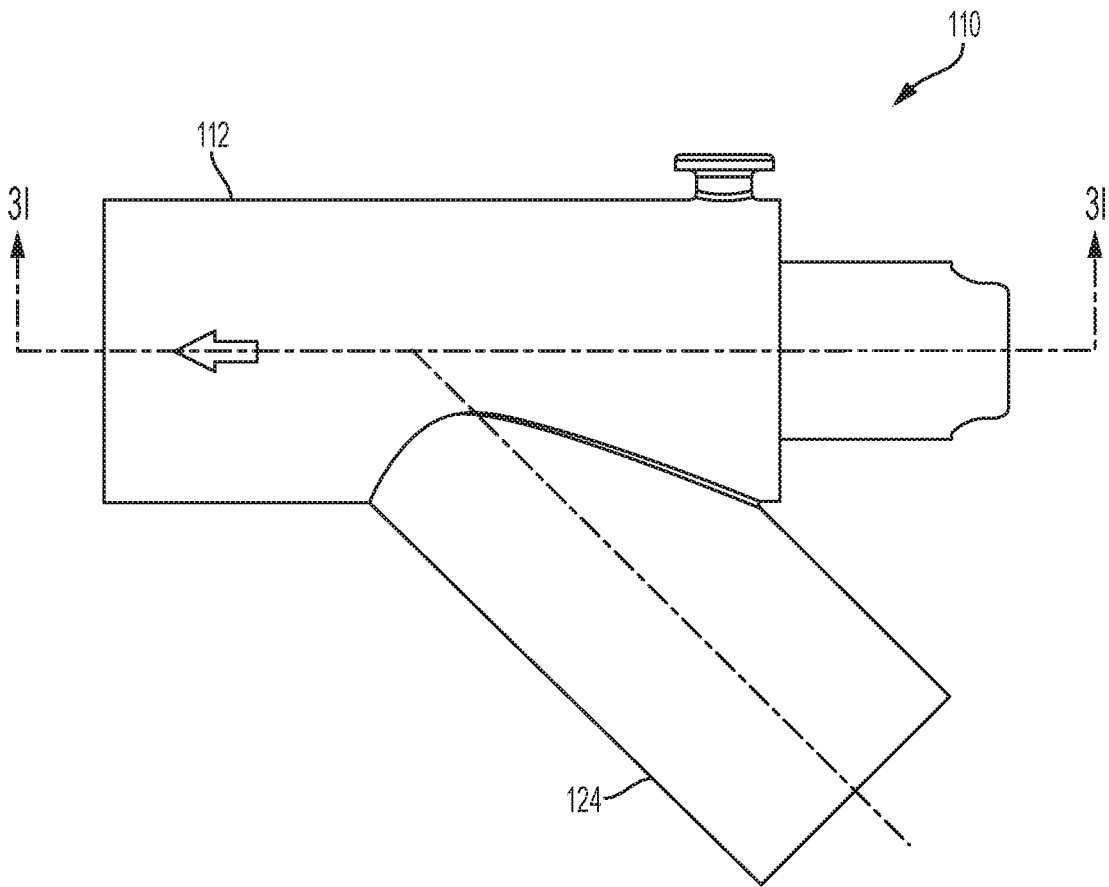
FIG. 3H is a top view of the adapter of FIG. 2B with the cap removed.
Figure 3I:
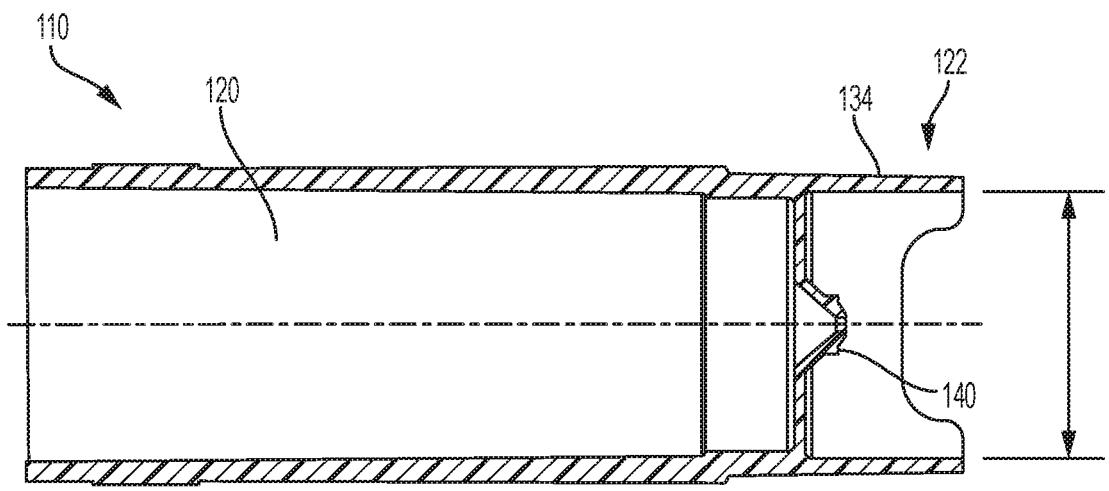
FIG. 3I is a cross sectional view of the adapter of FIG. 3H taken through a plane extending along line 3I-3I of FIG. 3H.
Figure 3J:
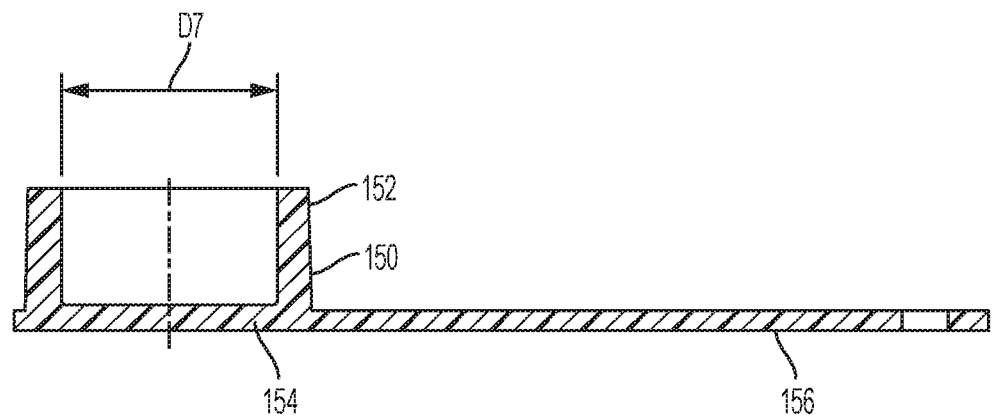
FIG. 3J is a cross sectional view of a cap for an adapter according to an example of the present invention.
Figure 3K:
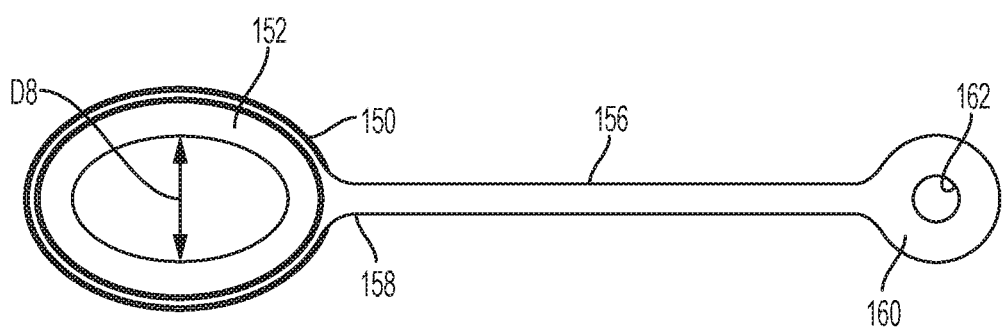
FIG. 3K is a bottom view of the cap of FIG. 3J.

The adapter 110 can be formed from a suitable rigid plastic material such as high density polyethylene, polystyrene, polystyrene-butadiene, and/or a polycarbonate material. In some examples, the adapter body 112 can be substantially clear or transparent so that a user can see the aerosolized medication dispersed from the inhaler mounted to the adapter 110 travel through the adapter 110 and enter the patient wye 218. By looking through the substantially clear or transparent sidewall of the adapter 110, a user can also confirm that different portions of the patent ventilation assembly 200 are correctly connected to the adapter 110. For example, a user can visually confirm that an inspiratory port 226 of a patient wye 218 is inserted into the adapter 110 an appropriate amount to form a suitable seal therebetween. Generally, the thickness 119 of the sidewall 118 of the adapter 110 can range from about 0.04 inches to about 0.08 inches, or about 1.0 mm to about 2.0 mm, or any size desired. The thickness of the sidewall can be uniform or tapered. For example, as shown in FIG. 3D, the thickness of the sidewall 118 may be tapered toward the exterior ends of the tube to facilitate removal of the adapter from the mold of an injection molding machine, to facilitate connection of breathing tubes thereto, or to facilitate connection to the inhaler. For example, the thickness 121 of the sidewall 118 in the region of the inhaler port 122 may be less than the thickness 119 of the sidewall 118 of the rest of the body 112 to accommodate the inhaler 250, such as, for example, about 0.03 inches to 0.07 inches, or any size desired.

The adapter 110 can be manufactured using various plastic manufacturing techniques as are known in the art. For example, the entire adapter 110 can be formed by a single-shot injection molding process in which the main body and angled tube are manufactured simultaneously in the same mold. In other examples, different portions of the adapter may be molded separately and connected together by, for example, an adhesive or plastic welding technique. In other examples, the adapter 110 can be manufactured by a two-shot injection molding process.

Figure 4A:
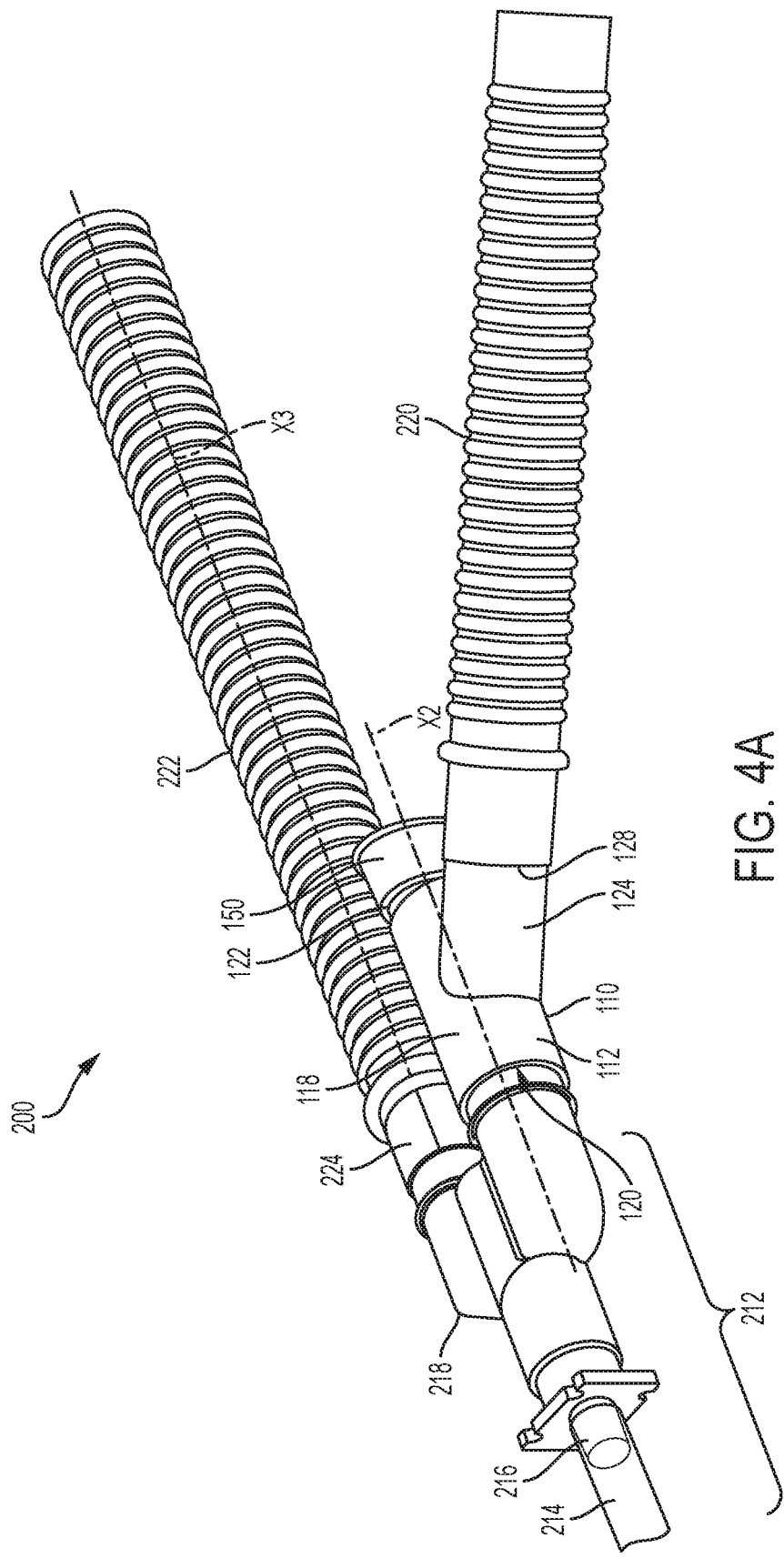
FIG. 4A is a perspective view of the adapter of FIGS. 2A and 2B connected in a patient ventilation assembly in a pre-use configuration according to an aspect of the disclosure.
Figure 4B:
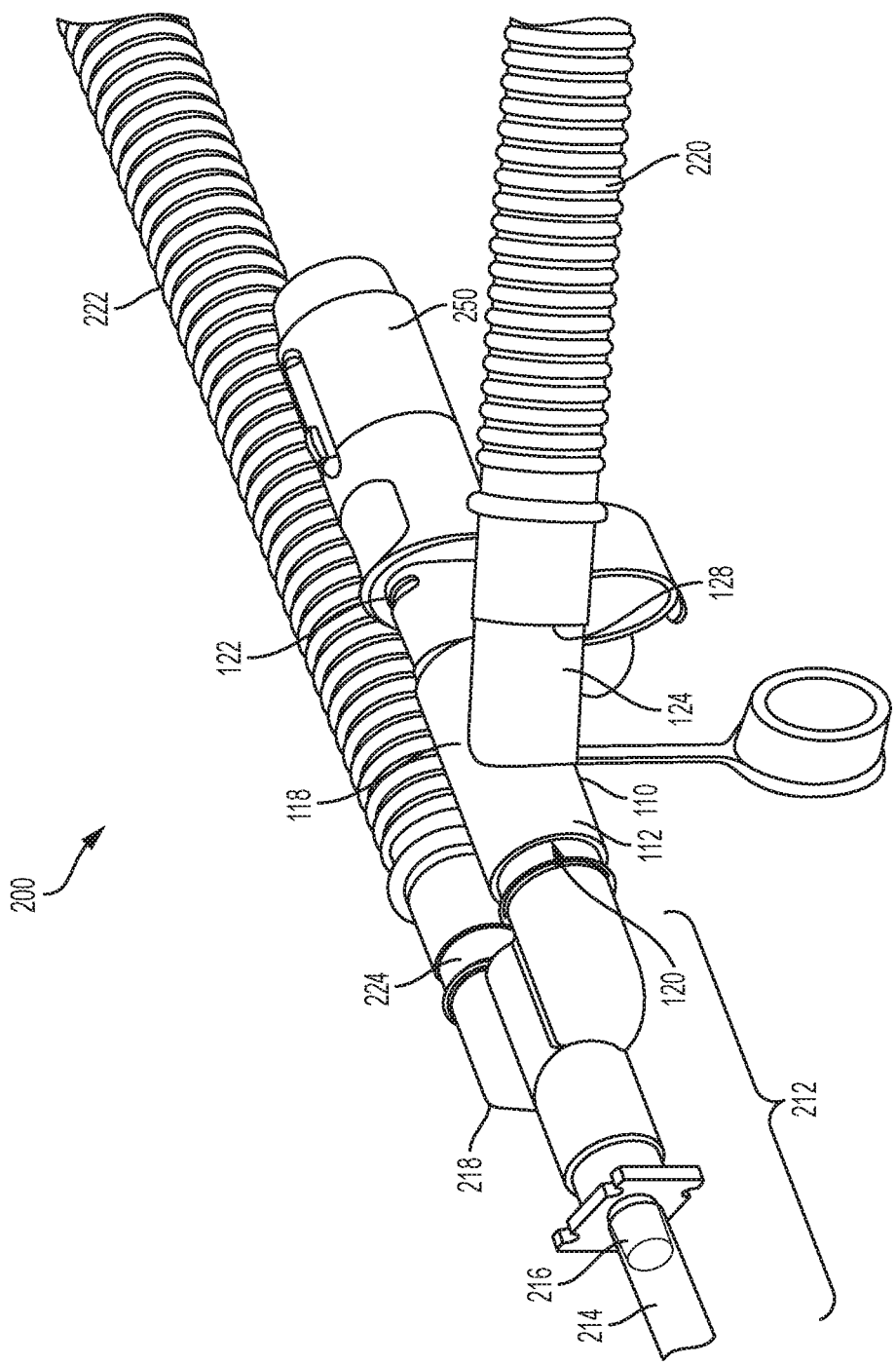
FIG. 4B is a perspective view of the patient ventilation assembly of FIG. 4A in an in-use configuration.

As shown in FIGS. 2A-4B and 7-9, the adapter 110 comprises an elongated hollow body 112 comprising an open proximal or first end 114, an open distal or second end 116 opposite the proximal or first end 114, and a sidewall 118 extending therebetween defining an airflow channel 120. Referring to FIG. 4B, the open proximal or first end 114 of the adapter body 112 is configured to receive the inspiratory port of the patient ventilation assembly. For example, the open proximal or first end 114 of the adapter body 112 may be sized so that an inspiratory port 226 of a Y-connector or patient wye 218 can be at least partially inserted in the first end 114 of the adapter 110, for example by a friction fit to inhibit leakage of inspiratory air from the breathing circuit to the outside environment. In order to interface with conventional patient breathing tubes or ventilation assemblies 200, the inner diameter D1 of the first or proximal end 114 of the adapter body can be about the size of standard medical tubing. For example, the proximal end 114 can have an inner diameter D1 (shown in FIGS. 3A and 3B) of about 15 mm to about 25 mm, or about 22 mm. The patient wye 218 or Y-connector is connected to patient portion 212 such as, for example, to an endotracheal tube 214 (shown in FIGS. 4A and 4B). Conventional endotracheal tubes are configured to be inserted through the patient's mouth into the trachea for providing breathing air to the lungs.

As shown in FIGS. 7-9, the open distal or second end 116 of the adapter body 112 is configured to be connected to the inhaler 250. For example, as shown in FIGS. 3B and 7-9, the second end 116 can include an inhaler port 122 extending therefrom for mounting the inhaler to the adapter 110. A length of the adapter 110 and, in particular, a length of airflow channel 120, is selected to permit good distribution of aerosolized particles dispensed from the inhaler. For example, the airflow channel 120 may have a length L4 (shown in FIG. 3B) of about 1.5 inches to about 3 inches, or about 1.8 inches to about 2.5 inches, or about 1.8 inches to about 2.2 inches, or about 2.5 inches, or any size desired. The adapter 110 may have a total longitudinal length L1 (shown in FIG. 3D) (including the adapter body 112 and inhaler port 122) of between about 2 inches and about 4 inches, or about 2.5 inches and about 3.5 inches, or about 3.0 inches, or any size desired.

The adapter 110 further comprises an elongated, tubular inspiratory branch 124 comprising an open first end 126 extending from an opening 130 (shown in FIG. 3B) in the sidewall 118 of the adapter body 112 and an open second end 128 configured to be connected to an inspiratory limb 220 or tube extending from a ventilator of the patient ventilation assembly. The opening 130 in the sidewall of the adapter body 112 can be of any shape, for example a generally elliptical or teardrop shaped opening to accommodate the inspiratory branch 124. The cross sectional area of the opening can range from about 0.2 square inches to about 1 square inch, or about 0.6 square inches, or any size desired.

In some examples, a length of a longest longitudinal side L3 (shown in FIG. 3A) of the inspiratory branch 124 is between about 1 inch and about 2.5 inches. As shown in FIGS. 4A, 4B and 6-9, the open distal or second end 128 of the inspiratory branch 124 is adapted to be inserted in an open end of the inspiratory limb 220 of the patient ventilation assembly. As shown in FIG. 3A, the external diameter D2 of the second end 128 of the inspiratory branch 124 can be, for example, a size of standard medical tubing used in breathing circuits and breathing tubes or any size desired. For example, the external diameter D2 of the second end 128 can be about 15 mm to 25 mm, or about 22 mm. An inner diameter D3 of the second end 128 can be about 12 mm to about 22 mm, for example, or any size desired.

In some examples, the inspiratory branch 124 extends from the adapter body 112 in a sloped or angled configuration. For example, a longitudinal central axis X1 (shown in FIGS. 3A and 3B) of the inspiratory branch 124 may be angled or sloped relative to a longitudinal central axis X2 (shown in FIGS. 3A and 3B) of the adapter body 112 at an angle α. The angle α can range from about 30 to about 60 degrees, or about 40 degrees to about 50 degrees, or at an angle of about 45 degrees.

The inhaler port 122 is adapted to receive a medication inhaler 250 configured to deliver metered doses of aerosolized fluid containing a medicinal agent. For example, the inhaler 250 can be a single-use or multi-use inhaler for delivering a mixture of ipratropium bromide and albuterol (e.g., a Combivent® Respimat® inhaler having a cartridge affixed thereto). The inhaler port 122 generally comprises an elongated sidewall 134 (shown in FIG. 3B) proximate the distal or second end 116 of the adapter body 112. As shown in FIG. 7, the sidewall 134 of the inhaler port 122 is configured to be inserted within a mouthpiece 252 of an inhaler 250. In order to be inserted in the mouthpiece 252 of the inhaler 250, the inhaler port 122 can have any cross-sectional shape, such as a circular or elliptical cross section, which corresponds in size and shape to an open end of the mouthpiece 252 of the inhaler 250. In some examples, the cross section of an elliptical opening has a major external diameter D4 (shown in FIG. 3G) which can range from about 0.5 inches to about 1.25 inches and, for example, may be between about 0.8 inches and about 0.95 inches, or any size desired. In some examples, the cross section of an elliptical opening has a minor external diameter D5 (shown in FIG. 3B) which can range from 0.3 inches to about 1.25 inches and, for example, may be between about 0.5 inches and about 0.75 inches or about 0.6 inch, or any size desired. In some examples, the cross section of a circular opening (not shown) has an external diameter D6 which can range from about 0.3 inches to about 1.25 inches and, for example, may be between about 0.5 inches and about 1 inch, or any size desired. The sidewall 134 thickness of the inhaler port 122 can be about 0.03 inches to about 0.07 inches, or any size desired. The sidewall 134 can be configured to cover air vents, if present, (shown in FIG. 7) on a discharge port of the inhaler, so that as much of the dispensed dose as possible is directed into the channel 120 of the adapter 110. The sidewall 134 can comprise one or more notches 135 to accommodate the inhaler. The depth of the notch 137 can range from about 0.1 to about 0.5 inches, or any size desired. The width 139 of the notch can range from about 0.25 to about 0.75 inches, or any size desired.

In some examples, the peripheral wall of the mouthpiece 252 of the inhaler 250 is inserted into a receiver defined by the sidewall 134 of the inhaler port 122. In order to receive the mouthpiece 252 of the inhaler 250, the inhaler port 122 can have any cross-sectional shape, such as a circular or elliptical cross section, which corresponds in size and shape to the exterior of the open end of the mouthpiece 252 of the inhaler 250. In some examples, the cross section of an elliptical opening has a major internal diameter D9 which can range from about 0.5 inches to about 1.25 inches and, for example, may be between about 0.8 inches and about 1 inch, or any size desired. In some examples, the cross section of an elliptical opening has a minor internal diameter D10 which can range from 0.3 to about 1.25 inches and, for example, may be between about 0.5 inches and about 0.75 inches or about 0.6 inches, or any size desired. In some examples, the cross section of a circular opening (not shown) has an internal diameter D11 which can range from about 0.3 inches to about 1.5 inches and, for example, may be between about 0.5 inches and about 1 inch, or any size desired. The sidewall 134 thickness of the inhaler port 122 can be about 0.03 inches to about 0.07 inches, or any size desired. The sidewall 134 can be configured to cover air vents, if present, on a discharge port of the inhaler, so that as much of the dispensed dose as possible is directed into the channel 120 of the adapter 110. The sidewall 134 can comprise one or more notches 135 to accommodate the inhaler. The depth of the notch 137 can range from about 0.1 to about 0.5 inches, or any size desired. The width 139 of the notch can range from about 0.25 to about 0.75 inches, or any size desired.

The inhaler port 122 further comprises an interior wall 136 (shown in FIGS. 3B and 3C) covering a portion of the open second end 116 of the adapter body 112. The interior wall 136 comprises an opening 138 configured to align with a discharge port or nozzle of the inhaler to permit fluid discharged from the inhaler to pass into the airflow channel 120 of the adapter body 112. The opening 138 can be circular, oval or any shape configured to align with the shape of the discharge port or nozzle of the inhaler. The diameter D12 of a circular opening 138 or oval opening can range from about 0.02 inches to about 0.1 inches, or about 0.05 inches to about 0.08 inches, or about 0.03 inches, or any size desired.

In some examples, the interior wall 136 further comprises a distally extending protrusion 140 extending about the opening 138. The protrusion 140 (shown in FIGS. 3B and 3C) can be sized for insertion into a corresponding depression of the inhaler surrounding the discharge port. The protrusion 140 and corresponding depression are aligned to ensure that the medication discharge port or nozzle aligns with the protrusion 140 so as not to impede flow of aerosolized medication therethrough.

In some examples, the adapter 110 further comprises a cap 150 (shown in FIGS. 2A, 2B, 3J and 3K) for covering the inhaler port 122 and, in particular, for sealing the inhaler port 122 to prevent air from leaking from the ventilation assembly, which would reduce air pressure delivered to the patient, when the inhaler is not attached to the port 122. In some examples, the cap 150 comprises an annular sidewall 152 configured to enclose the sidewall 134 of the inhaler port 122. The cap 150 further comprises a flat top or cover 154 extending across an open proximal end of the sidewall 152 for closing off and sealing the inhaler port 122. The top or cover 154 of the cap 150 can generally correspond in shape to the open end of the inhaler port 122. For example, the top of cover of the cap can be configured to accommodate and seal the inhaler port 122 opening. For example, the sidewall 152 of the cap 150 can be an elliptical shape having a major internal diameter D7 (shown in FIG. 3K) of about 0.5 to about 1.25 inches or about 0.8 inches and a minor internal diameter D8 of about 0.3 to 1.25 inches, or any size desired. The thickness of the sidewall can range from about 0.03 inches to about 0.3 inches, or about 0.1 inches to about 0.2 inches, or any size desired. The cap 150 can provide a snug fit about the exterior of the sidewall of the inhaler port to prevent air from the breathing circuit from escaping into the exterior environment.

The cap 150 can be formed from a variety of materials including, for example, plastics, rubbers, or metals. In some examples, the cap 150 is formed from a flexible thermoplastic rubber material, such as a thermoplastic polyurethane, olefins, or silicone. The thermoplastic rubber is capable of releasably adhering to the sidewall 134 of the inhaler port 122 to form a secure connection therewith. In some examples, the cap 150 further comprises a tether 156 having a first end 158 connected to the cap 150 and a second end 160 connected to the adapter body 112. For example, the second end 160 of the tether 156 may comprise a loop 162 configured to receive a corresponding protrusion 164 extending from the adapter body 112, such that the cap 150 is rotatably secured to the adapter body 112 through the tether 156. As a result of the tether 156, a user can merely let go of the cap 150 after it is removed from the inhaler port 122. The cap 150 then hangs freely from the adapter body 112 as the inhaler is being used to provide medication to the patient, as shown in FIG. 4B. After the medication is delivered and the inhaler is removed from the inhaler port 122, the user can replace the cap 150 by pressing it onto the inhaler port 122.

Patient Ventilation Assembly and Breathing Circuit

According to an example of the disclosure, a patient ventilation assembly 200 or breathing tube is provided. As shown in FIGS. 4A and 4B, the ventilation assembly 200 is configured to deliver a dose of aerosolized medication from a metered dose inhaler 250 (shown in FIG. 4B) to the patient through medical tubing and connecting elements of the ventilation assembly 200 or breathing tube. Specifically, the assembly 200 or breathing tube comprises the above-described adapter 110 which places the metered dose inhaler 250 in fluid communication with the patient's lungs through an airflow path defined by the tubing of the ventilation assembly 200.

As shown in FIGS. 4A and 4B, the ventilation assembly 200 comprises a patient portion 212, such as an endotracheal tube 214, having a proximal end (not shown) configured to be positioned in the trachea of a patient for delivering breathing air to the patient's lungs, and a distal end 216 connected to a branched connector, such as a patient wye 218. The patient wye 218 can be a commercially available patient wye connector as is known in the art, such as a plastic single-use or reusable wye connector. For example, the patient wye 218 can be formed from a polycarbonate material. In general, the patient wye 218 is an open, three port connector that places the patient portion 212 of the assembly 200 in communication with an inspiratory limb 220 and an expiratory limb 222 of the ventilation assembly 200. The assembly 200 further comprises the adapter 110 for connecting the inhaler 250 to the assembly 200 and, in particular, for establishing fluid communication from the inhaler 250 to the patient's endotracheal tube 214.

As in previously described examples, the adapter 110 shown in FIGS. 4A and 4B comprises the elongated hollow body 112 defining the airflow channel 120; an inhaler port 122 extending from the adapter body 112; and the inspiratory branch 124 extending from an opening in a sidewall 118 of the adapter body 112. As in previously described examples, a longitudinal axis X1 (shown in FIGS. 3A and 3B) of the inspiratory branch 124 is sloped or angled relative to a longitudinal axis X2 (shown in FIGS. 3A and 3B) of the adapter body 112.

As shown in FIGS. 4A and 4B, the inspiratory limb 220 is connected to the inspiratory branch 124 of the adapter 110. For example, as previously described, the inspiratory branch 124 may be inserted in the inspiratory limb 220. In order for this configuration to be possible, the outer diameter of the inspiratory branch 124 of the adapter 110 is substantially equal to or slightly less than an inner diameter of standard medical tubing. The ventilation assembly 200 further comprises the expiratory limb 222 extending from an expiratory port 224 of the patient wye 218. The inspiratory limb 220 and the expiratory limb 222 can be formed from conventional medical tubing commonly used in breathing circuits and breathing tubes. For example, the medical tubing can be corrugated tubing formed from a flexible plastic material. The tubing can have an inner diameter of about 15 mm to about 25 mm, or about 22 mm. The tubing can be formed from various plastic materials including silicone, ethylene vinyl acetate, polyethylene, and similar materials.

In some examples, the arrangement of the medical tubing (inspiratory limb 220 and expiratory limb 222), patient wye 218, and inline adapter 110 is selected to permit easy set-up and storage of ventilation assembly components. In addition, the medical tubing is arranged to avoid forming kinks in the tubing and so that the tubing does not interfere with other devices being used to provide care to the patient. For example, as shown in FIGS. 4A and 4B, the expiratory limb 222 of the ventilation assembly 200 and adapter 110 are positioned in a substantially parallel arrangement in which a longitudinal axis X3 (shown in FIG. 4A) of the expiratory limb 222 is substantially parallel to the longitudinal axis X2 (shown in FIGS. 3A and 4A) of the adapter body 112.

In some examples, as shown in FIG. 5, the ventilation assembly 200 and adapter 110 are part of a breathing circuit 300 for providing breathing air from a mechanical ventilator 310 to a patient 312. As shown in FIG. 5, the breathing circuit 300 comprises the ventilator 310, which comprises an outflow port 314 and an inflow port 316. The mechanical ventilator 310 can be configured to provide positive pressure ventilation to the patient by generating continuous or pulsed ventilations through an inspiratory limb 220 of the ventilation assembly 200. The inspiratory limb 220 of the ventilation assembly 200 or breathing tube is connected to the outflow port 314 of the ventilator 310. The expiratory limb 222 of the ventilation assembly 200 is connected to the inflow port 316. In use, the ventilator 310 is configured to provide breathing air to the patient through the ventilation assembly 200 and adapter 110. Specifically, air is expelled from the ventilator 310 through the outflow port 314 into the inspiratory limb 220 of the ventilation assembly 200 in the direction of arrow A1 in FIG. 5. In a similar manner, air exhaled by the patient 312 passes through the patient wye 218 and expiratory limb 222 of the assembly 200 in the direction of arrow A2 in FIG. 5. The exhaled air is then introduced to the ventilator 310 through the inflow port 316.

Method for Delivering a Dose to a Patient

Referring now to FIG. 7, according to another aspect of the disclosure, a method for delivering a metered dose of an aerosolized medication to a patient through an inline adapter 110 and patient ventilation assembly 200 or breathing tube is disclosed herein. The adapter 110 can remain connected to the patient ventilation assembly 200 for the entire lifespan or use period of the ventilation assembly 200 or breathing tube. For example, current Center for Disease Control guidelines recommend replacing the breathing tube every 14 days. The inhaler port 122 of the adapter 110 is designed to be covered by the cap 150 when not in use and, in particular, when the inhaler 250 is not connected to the adapter 110. The inhaler 250 can be a single-dose or multi-dose inhaler depending on the needs of a particular patient. It is generally expected that the inhaler 250 and/or cartridge will be discarded after use of one or more of the doses therein.

Figure 6:
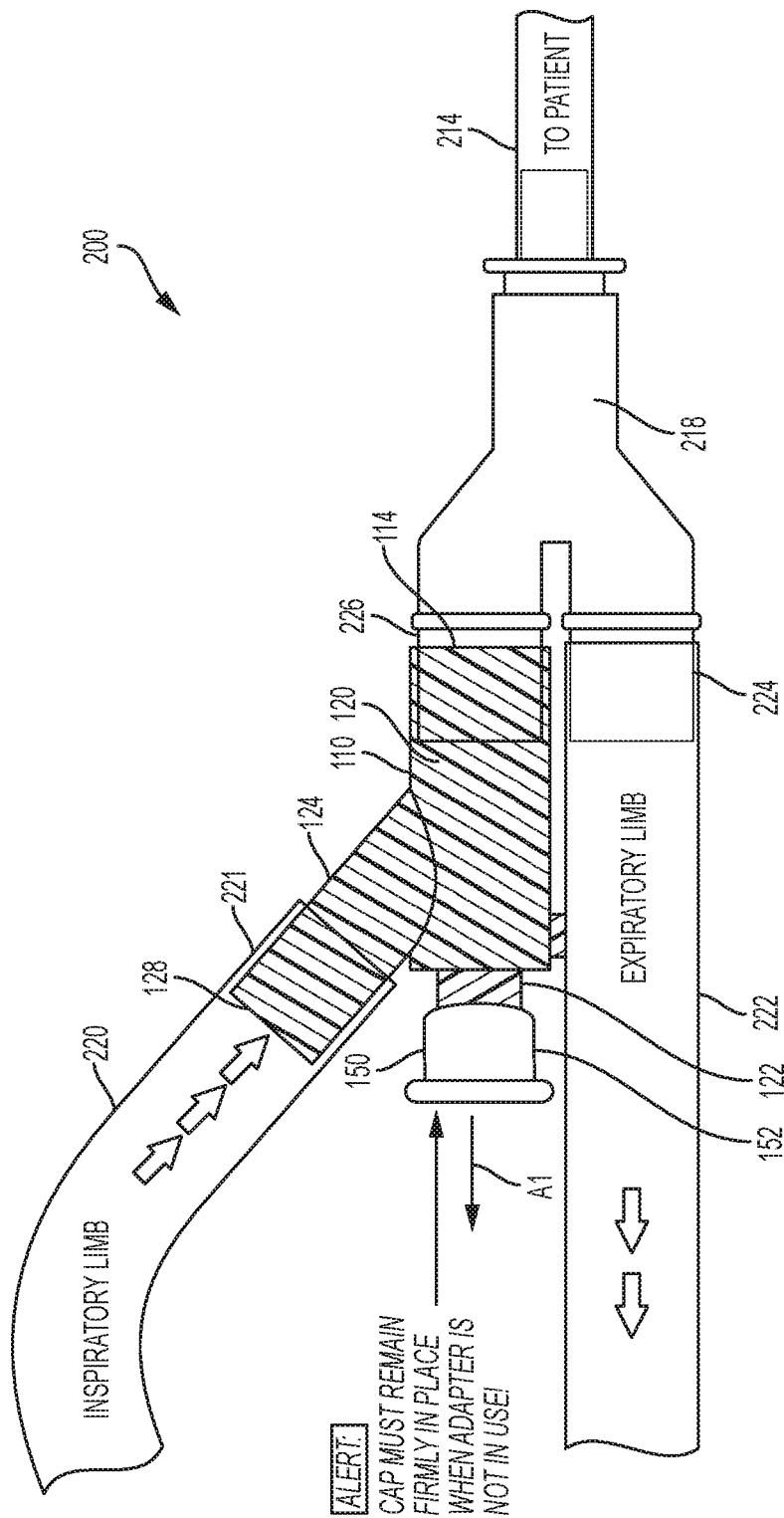
FIG. 6 is a schematic drawing of the assembly of FIGS. 4A and 4B in a pre-use configuration.

The method comprises attaching an inline adapter 110 between an inspiratory port 226 of a patient wye 218 and an inspiratory limb 220 connected to a ventilator 310 (shown in FIG. 5). As shown in FIGS. 6 and 7, for example, a user may insert the inspiratory port 226 of the patient wye 218 into a first or proximal end 114 of the adapter 110 to place an airflow channel 120 of the adapter 110 in fluid communication with the patient wye 218 and thereby to the patient. The user may then insert a distal or second end 128 of the inspiratory branch 124 of the adapter 110 into a proximal end 221 of the inspiratory limb 220. In a similar manner, the user may also connect the expiratory limb 222 to the corresponding expiratory port 224 of the patient wye 218 by, for example, inserting the expiratory port 224 of the patient wye 218 into the proximal end of the expiratory limb 222.

Once the adapter 110 and medical tubing of the ventilation assembly 200 are assembled and, when ready to provide a dose of medication to the patient, the user may prepare an inhaler 250 for use in a conventional manner. For example, the user may remove a cap or packaging from the inhaler 250. The user may prime the inhaler 250 by rotating the primer, or holding the inhaler in an upright position (e.g., with a mouthpiece 252 of the inhaler pointing upwards) and pressing a drug release button 254 or another prime button in accordance with instructions provided by the manufacturer of the inhaler 250. Once the inhaler 250 is primed and ready for use, the user removes the cap 150 from the inhaler port of the adapter 110 by, for example, holding the adapter body 112 in one hand, grasping the cap 150 in the other hand, and pulling the cap away from the adapter body 112 so that the annular sidewall 152 of the cap 150 slides away from the sidewall 134 of the inhaler port 122, in the direction of arrow A1 (shown in FIG. 6). Once the cap 150 is removed, the user connects the inhaler 250 to the inhaler port 122. For example, the user may press the inhaler 250 in the direction of arrow A2, shown in FIG. 7, such that the sidewall 134 of the inhaler port 122 slides into the mouthpiece 252 of the inhaler 250. As previously described, the sidewall 134 of the inhaler port 122 is configured to extend into the mouthpiece of the inhaler 250 to cover air vents 256 of the inhaler 250 to ensure that medication discharged by the inhaler 250 passes through a discharge port of the inhaler 250 and into the airflow channel 120 of the adapter body 112. In some examples, the inhaler mouthpiece 252 and/or inhaler port 122 can comprise a friction fit or snap fit connector or similar mechanism for removably attaching, connecting or locking the inhaler 250 to the inhaler port 122 in the desired position. In other examples, the connection between the mouthpiece 252 and inhaler port 122 can be a luer lock connection or a threaded or screw-type connection, as are known in the art.

Once the inhaler 250 is connected to the inhaler port 122, as shown in FIG. 8, the user may actuate the inhaler 250 to deliver the dose of medication by, for example, pressing the dose release button 254. Preferably, the dose can be delivered at the onset of inspiration so that the majority of the full dosage is administered to the patient. In some examples, the user may remove the inhaler to prime the inhaler for the next dose, for example by rotating the primer on the inhaler, before re-attaching the inhaler to the inhaler port 122, or the inhaler may be primed while still attached to the patient tubing.

Pressing the dose release button 254 causes the inhaler 250 to release an aerosolized dose of the medication through a discharge port 264. The released dose is directed to the airflow channel 120 of the adapter body 112 as shown in FIG. 9. In examples in which the adapter 110 comprises a substantially clear or transparent material, the user can see the dose of administered medication pass through the adapter body 112. If the medication is not visible immediately after dosing, the user may check the inhaler 250 to ensure that it is properly connected to the inhaler port 122 and properly primed.

As shown in FIGS. 8 and 9, breathing air provided by the ventilator, which enters the adapter channel 120 through the inspiratory branch 124, mixes with the dispersed medication in the airflow channel 120. The breathing air and dispersed medication is directed through the proximal or first end 114 of the adapter 110 and into the patient wye 218. The breathing air and dose of medication continues from the patient wye 218 into the patient's endotracheal tube 214. The dose of medication 266 passes through the endotracheal tube 214 to the patient. In some examples, multiple doses of medication can be delivered. For example, the user may press the dose release button 254 of the inhaler 250 to release a first medication dose. The user may wait a predetermined period of time and then prime and press the dose release button 254 again to release a second metered dose of the medication.

Once all of the prescribed doses of the medication have been delivered from the inhaler 250 to the patient or the medication is no longer needed, the user may remove the inhaler 250 from the inhaler port 122 by grasping the inhaler 250 and pulling it away from the inhaler port 122 in the direction of arrow A3 (shown in FIGS. 8 and 9). The user then reattaches the cap 150 to the inhaler port 122 to return the adapter 110 and ventilation assembly 200 to the pre-use position, as shown in FIG. 6.

EXPERIMENTAL EXAMPLE

In order to demonstrate that the adapter disclosed herein delivers medication to a patient in appropriate quantities, the following experimental test was performed. A Combivent® Respimat® metered dose inhaler and cartridge were mounted to the adapter. Medication was discharged from the inhaler and an amount of aerosolized fluid which passed through the adapter was collected. The inhaler was used with three sample adapters to account for possible differences in manufacturing. Three tests were performed per adapter sample for a total of nine measurements per medication and output variable. Results from the nine tests were either averaged or provided as a range. The test results for an example of the presently disclosed adapter shown in FIGS. 2A-3K are shown in Table 1. This adapter had a diameter D1 of about 0.9 inches, a diameter D2 of about 0.9 inches, a diameter D3 of about 0.75 inches, a diameter D4 of about 0.95 inches, a diameter D5 of about 0.55 inches, a length L1 of about 2.95 inches, a length L3 of about 1.75 inches, a length L4 of about 2.4 inches, and opening in the interior wall of about 0.05 inches.

TABLE 1

Present adapter with sloped inspiratory branch

|  | Albuterol | Ipratropium Bromide |
|---|---|---|
| Total delivered dose from adapter (µg)[1] | 58.1-67.2 | 11.4-13.9 |
| % Reduction in Total Delivered Dose compared to Combivent Respimat SMI alone | 27.8% | 34.0% |
| Respirable Particle Mass from Adapter (µg. 0.5-5 µm)[1] | 24.7-28.5 | 5.0-5.9 |
| Respirable Fraction (µg. 0.5-5 µm) | 42.4% | 43.7% |
| % Reduction in Respirable Dose compared to Combivent Respimat SMI alone | 47.5% | 50.4% |
| Coarse Particle Dose (µg. >4.7 µm)[1] | 22.3-28.8 | 4.0-6.3 |
| Particle Fraction >4.7 µm | 40.8% | 40.5% |
| Fine Particle Dose (µg. <4.7 µm)[1] | 35.1-39.1 | 6.8-8.1 |
| Particle Fraction <4.7 µm | 59.2% | 59.5% |
| Extra-Fine Particle Dose (µg. <1.0 µm)[1] | 17.7-20.6 | 3.5-4.2 |
| Particle Fraction <1.0 µm | 30.5% | 30.2% |
| Mass-Median Aerosol Diameter (MMAD) (µm)[1] | 1.4-1.7 | 1.4-1.7 |
| Geometric Standard Deviation (GSD)[1] | 3.8-4.6 | 3.9-4.6 |

[1]95% confidence intervals.

There is an unmet need in the art for an inline adaptor to deliver medicament in a straight line through the adapter from a Combivent® Respimat® type of metered dose inhaler and cartridge to a breathing circuit. As shown by the experimental results, the tested example of the presently disclosed adapter successfully provides an average of about 72.2% of the dosage of albuterol and about 66% of the dosage of Ipratropium Bromide normally delivered from a Combivent® Respimat® metered dose inhaler and cartridge without use of an adapter.

The preceding examples and embodiments of the invention have been described with reference to various examples. Modifications and alterations will occur to others upon reading and understanding the foregoing examples. Accordingly, the foregoing examples are not to be construed as limiting the disclosure.

What is claimed is:

1. An inline adapter, comprising:
an elongated hollow body comprising an open first end configured to be connected to an inspiratory port of a patient ventilation assembly, an open second end opposite the first end, and a sidewall extending therebetween defining an airflow channel;
an inhaler port extending from the open second end of the elongated hollow body configured to be connected to an inhaler, the inhaler port comprising: an annular sidewall extending from the open second end of the elongated hollow body defining a channel; and a wall extending across the channel, the wall comprising a tapered portion defining an opening through the wall, the opening being configured to align with a discharge port of the inhaler to permit fluid discharged from the inhaler to pass into the airflow channel of the elongated hollow body, and the tapered portion of the wall comprising a first end portion having a first inner diameter and a second end portion having a second inner diameter that is smaller than the first inner diameter, wherein the first end portion is closer to the elongated hollow body than is the second portion; and
an inspiratory branch comprising an open first end extending from an opening in the sidewall of the elongated hollow body and an open second end configured to be connected to an inspiratory limb of the patient ventilation assembly,
wherein a longitudinal central axis of the inspiratory branch is angled relative to a longitudinal central axis of the elongated hollow body.

2. The adapter of claim 1, wherein the longitudinal central axis of the inspiratory branch forms an angle of between about 30 degrees and about 60 degrees relative to the longitudinal central axis of the elongated hollow body.

3. The adapter of claim 1, wherein the annular sidewall of the inhaler port is configured to be received within a mouthpiece of the inhaler and to cover air vents on the mouthpiece of the inhaler.

4. The adapter of claim 3, wherein the annular sidewall of the inhaler port comprises an elliptical cross section, and wherein the elliptical cross section has a major external diameter D4 ranging from about 0.5 inches to about 1.25 inches.

5. The adapter of claim 1, wherein the inspiratory port of the patient ventilation assembly is an inspiratory port of a patient wye of the patient ventilation assembly, and wherein the open first end of the elongated hollow body is configured to receive the inspiratory port of the patient wye of the patient ventilation assembly.

6. The adapter of claim 1, wherein the open second end of the inspiratory branch of the adapter is configured to be inserted in an open end of the inspiratory limb of the patient ventilation assembly.

7. The adapter of claim 1, wherein an outer diameter of the open second end of the inspiratory branch of the adapter is about equal to an inner diameter of the open first end of the elongated hollow body.

8. The adapter of claim 1, wherein a total longitudinal length of the adapter ranges from about 2 inches to about 4 inches, and wherein a length of a longest longitudinal side of the inspiratory branch ranges from about 1 inch to about 2.5 inches.

9. The adapter of claim 1, wherein the opening in the sidewall of the elongated hollow body extending to the inspiratory branch is an elliptical opening.

10. The adapter of claim 1, further comprising a cap removably connected to the inhaler port.

11. The adapter of claim 1, wherein the wall extending across the channel of the inhaler port further comprises an annular flange portion extending from an end of the tapered portion of the wall to the annular sidewall of the inhaler port, and
wherein the annular flange portion is positioned closer to the open second end of the elongated hollow body than is the opening defined by the tapered portion of the wall.

12. The adapter of claim 11, wherein the tapered portion of the wall defines a tapered cavity which is widest at the end extending to the annular flange portion and narrowest at an end which defines the opening through the wall, and
wherein the tapered portion is positioned such that, when the inhaler is connected to the inhaler port, fluid ejected from the inhaler passes into the tapered cavity through the opening defined by the tapered portion of the wall.

13. The adapter of claim 11, wherein the tapered portion of the wall of the inhaler port comprises an annular tapered inner surface, an annular tapered outer surface, and an annular protrusion extending from the annular tapered outer surface positioned to engage the discharge port of the inhaler.

14. The adapter of claim 13, wherein the opening defined by the wall of the inhaler port has a diameter of from 0.02 inch to 0.1 inch.

15. The adapter of claim 1, wherein the elongated hollow body, the annular sidewall of the inhaler port, and the wall extending across the channel defined by the annular sidewall are formed from a rigid plastic material.

16. A ventilation assembly for providing breathing air and aerosolized medication to a patient, comprising:
an inspiratory limb comprising medical tubing configured to be connected to an outflow port of a mechanical ventilator device;
an expiratory limb comprising medical tubing configured to be connected to an inflow port of the ventilator device;
a patient wye comprising a patient port connected to a patient portion of the ventilation assembly, an expiratory port connected to the expiratory limb, and an inspiratory port; and
an inline aerosol adapter connected between the inspiratory port of the patient wye and the inspiratory limb, the adapter comprising:
an elongated hollow body comprising an open first end connected to the inspiratory port of the patient wye, an open second end opposite the first end, and a sidewall extending therebetween defining an airflow channel in fluid communication with an airflow channel of the patient wye;
an inhaler port extending from the open second end of the elongated hollow body configured to be connected to an inhaler, the inhaler port comprising: an annular sidewall extending from the open second end of the elongated hollow body defining a channel; and a wall extending across the channel, the wall comprising a tapered portion defining an opening through the wall, the opening being configured to align with a discharge port of the inhaler to permit fluid discharged from the inhaler to pass into the airflow channel of the elongated hollow body, and the tapered portion of the wall comprising a first end portion having a first inner diameter and a second end portion having a second inner diameter that is smaller than the first inner diameter, wherein the first end portion is closer to the elongated hollow body than is the second portion; and an inspiratory branch comprising an open first end extending from an opening in the sidewall of the elongated hollow body and an open second end connected to the inspiratory limb, wherein a longitudinal central axis of the inspiratory branch is angled relative to a longitudinal central axis of the elongated hollow body.

17. The assembly of claim 16, wherein a longitudinal central axis of the expiratory port is substantially parallel to the longitudinal central axis of the elongated hollow body.

18. The assembly of claim 16, further comprising the inhaler comprising a mouthpiece configured to be received within the annular sidewall of the inhaler port, wherein the inhaler comprises a single-dose inhaler or a multi-dose inhaler comprising an indicator for indicating doses of medication remaining in the inhaler.

19. The assembly of claim 18, wherein the mouthpiece of the inhaler comprises air vents, and wherein the annular sidewall of the inhaler port of the adapter covers the air vents when the inhaler is connected to the inhaler port.

20. The assembly of claim 16, wherein the elongated hollow body, the annular sidewall of the inhaler port, and the wall extending across the channel defined by the annular sidewall are formed from a rigid plastic material, wherein the wall extending across the channel of the inhaler port further comprises an annular flange portion extending from an end of the tapered portion of the wall to the annular sidewall of the inhaler port, wherein the annular flange portion is positioned closer to the open second end of the elongated hollow body than is the opening defined by the tapered portion of the wall, wherein the tapered portion of the wall defines a tapered cavity which is widest at the end extending to the annular flange portion and narrowest at an end which defines the opening through the wall, wherein the tapered portion is positioned such that, when the inhaler is connected to the inhaler port, fluid ejected from the inhaler passes into the tapered cavity through the opening defined by the tapered portion of the wall, and wherein the tapered portion of the wall of the inhaler port comprises an annular tapered inner surface, an annular tapered outer surface, and an annular protrusion extending from the annular tapered outer surface positioned to engage the discharge port of the inhaler.

21. A method of providing aerosolized medication to a patient through a patient ventilation assembly, comprising:

attaching an inline adapter between an inspiratory port of a patient wye and an inspiratory limb of a ventilation assembly comprising tubing configured to be connected to a ventilator, wherein the adapter comprises:

an elongated hollow body comprising an open first end configured to be connected to the inspiratory port of the patient wye, an open second end opposite the first end, and a sidewall extending therebetween defining an airflow channel;

an inhaler port extending from the open second end of the elongated hollow body configured to be connected to an inhaler, the inhaler port comprising: an annular sidewall extending from the open second end of the elongated hollow body defining a channel; and a wall extending across the channel, the wall comprising a tapered portion comprising an annular tapered inner surface and an annular tapered outer surface, the surfaces defining an opening through the wall, the opening being configured to align with a discharge port of the inhaler to permit fluid discharged from the inhaler to pass into the airflow channel of the elongated hollow body, a first end portion having a first inner diameter, a second end portion having a second inner diameter that is smaller than the first inner diameter, wherein the first end portion is closer to the elongated hollow body than is the second portion, and an annular protrusion extending from the annular tapered outer surface configured to engage the discharge port of the inhaler; and an inspiratory branch comprising an open first end extending from an opening in the sidewall of the elongated hollow body and an open second end configured to be connected to the inspiratory limb of the ventilation assembly, wherein a longitudinal central axis of the inspiratory branch is angled relative to a longitudinal central axis of the elongated hollow body;

connecting the inhaler to the inhaler port of the adapter, such that the discharge port of the inhaler engages the annular protrusion of the tapered portion of the inhaler port;

actuating the ventilator to provide breathing air to the patient through the ventilation assembly and adapter; and actuating a dose release actuator of the inhaler to provide aerosolized medication to the patient through the adapter and ventilation assembly.

* * * * *